United States Patent [19]

Seshadri et al.

[11] Patent Number: 6,100,445
[45] Date of Patent: Aug. 8, 2000

[54] TRANSGENIC KNOCKOUT MOUSE HAVING FUNCTIONALLY DISRUPTED INTERLEUKIN-1β CONVERTING ENZYME GENE

[75] Inventors: Tara Seshadri, Sturbridge; Ping Li, Wellesley; Hamish Allen; Subhashis Banerjee, both of Shrewsbury; Michael Paskind, Cambridge, all of Mass.

[73] Assignee: BASF Aktiengesellschaft, Germany

[21] Appl. No.: 08/954,536

[22] Filed: Oct. 20, 1997

Related U.S. Application Data

[63] Continuation of application No. 08/323,490, Oct. 14, 1994, abandoned.

[51] Int. Cl.[7] .............................. C12N 5/00; C12N 15/00; C07H 21/04; A01K 67/027
[52] U.S. Cl. ................................ 800/18; 800/13; 800/22; 800/25; 435/69.1; 435/320.1; 435/325; 435/463; 435/455; 536/23.1; 536/23.2
[58] Field of Search .................................. 435/69.1, 69.7, 435/172.1, 172.3, 354, 356, 320.1, 455, 14, 32, 52, 55, 66, 70, 71, 325, 463; 536/23.1, 23.2; 800/13, 22, 25, 18

[56] References Cited

FOREIGN PATENT DOCUMENTS

| | | |
|---|---|---|
| 42 28 162 | 1/1994 | Germany . |
| 1730594 | 4/1992 | U.S.S.R. . |
| WO 91/01140 | 2/1991 | WIPO . |
| WO 91/15577 | 10/1991 | WIPO . |
| WO 91/19796 | 12/1991 | WIPO . |
| WO 92/11874 | 7/1992 | WIPO . |
| WO 92/20808 | 11/1992 | WIPO . |
| WO 93/04169 | 3/1993 | WIPO . |
| WO 93/05071 | 3/1993 | WIPO . |
| WO 94/00154 | 1/1994 | WIPO . |
| WO 94/06906 | 3/1994 | WIPO . |
| WO 94/21784 | 9/1994 | WIPO . |

OTHER PUBLICATIONS

Li, et al, Cell, vol. 80, pp. 401–411, Feb. 10, 1995.
Houdebine, Journal of Biotechnology 34, pp. 269–287, May 1994.
Cerretti et al., Genomics 20, pp. 468–473, 1994.
Molineaux Proc. Natl. Acad. Sci. USA vol. 90, pp. 1809–1813, Mar. 1993.
Koshura, Proc. Natl. Acad. Sci. USA vol. 86. pp 5227–5231, Jul. 1989.
Webster's II New Riverside University Dictionary 1984 Houghton Mifflin Company.
Silver et al. 1985 Molecular and Cellular Biology 5(3): 518–528.
Capecchi, M., "The New Mouse Genetics: Altering the Genome by Gene Targeting," *Trends in Genetics*, vol. 5, No. 3, 70–76 (1989).
Medline Abstract No. 94360969, Erdo, F., et al., "Measurement of Interleukin–1 Liberation in Zymosan Air–pouch Exudate in Mice," *Agents and Actions*, vol. 41, No. 1–2, pp. 93–95 (1994).

Black, Roy A. et al. (1989) "Activation of interleukin–1β by a co–induced protease" FEB 247(2): 386–390.
Black, Roy A. et al. (1989) "A Pre–aspartate–specific Protease from Human Leukocytes That Cleaves Pro–interleukin–1β" J. Biol. Chem. 264(10): 5323–5326.
Bradley, A. (1991) "Modifying the mammalian genome by gene targeting" *Current Opinion in Biotechnology* 2: 823–829.
Capecchi, M.R. (1989) "Altering the Genome by Homologous Recombination" *Science* 244: 1288–1292.
Casano, F.J. et al. (1994) "Structure and Complete Nucleotide Sequence of the Murine Gene Encoding Interleukin–1β Converting Enzyme (ICE)" *Genomics* 20: 474–481.
Cerretti, D.P. et al. (1992) "Molecular Cloning of the Interleukin–1β Converting Enzyme" *Science* 256: 97–100.
Fernandes–Alnemri, T. et al. (1994) "CPP32, a Novel Human Apoptotic Protein with Homology to *Caenorhabditis elegans* Cell Death Protein Ced–3 and Mammalian Interleukin–1β–converting Enzyme" *J. Biol. Chem.* 269(49):30761–30764.
Kumar, S. et al. (1994) "Induction of apoptosis by the mouse Nedd2 gene, which encodes a protein similar to the product of the *Caenorhabditis elegans* cell death gene ced–3 and the mammalian IL–1β–converting enzyme" *Genes & Development* 8: 1613–1626.
Mansour, S.L. et al. (1988) "Disruption of the photo–oncogene int–2 in mouse embryo–derived stem cells; a general strategy for targeting mutations to non–selectable genes" *Nature* 336: 348–352.
Miura, M. et al. (1993) "Induction of Apoptosis in Fibroblasts by IL–1β–Converting Enzyme, a Mammalian Homolog of the C. elegans Cell Death Gene ced–3" *Cell* 75: 653–660.
Nett, M.A. et al. (1992) "Molecular Cloning of the Murine IL–1β Converting Enzyme cDNA" *J. Immunol.* 149(10): 3254–3259.

(List continued on next page.)

*Primary Examiner*—Karen M. Hauda
*Assistant Examiner*—Janet M Kerr
*Attorney, Agent, or Firm*—Lahive & Cockfield, LLP; Giulio A. DeConti, Jr.; Catherine J. Kara

[57] ABSTRACT

A transgenic mouse having somatic and germ cells in which at least one allele of an endogenous interleukin-1β converting enzyme (ICE) gene is functionally disrupted is provided. The mouse may be heterozygous or, more preferably, homozygous for the ICE gene disruption. In homozygous mice, secretion of mature interleukin-1β and interleukin-1α is substantially reduced relative to non-mutant mice. The mice of the invention can be used as positive controls to evaluate the efficacy of ICE inhibitors and to identify disease conditions that can be treated with ICE inhibitors. A transgenic mouse having functionally disrupted endogenous ICE genes but which has been reconstituted with a human ICE gene is also provided. This mouse can be used to identify agents that inhibit human ICE in vivo. Nucleic acid constructs for functionally disrupting an endogenous ICE gene in a host cell, recombinant vectors including the nucleic acid construct, and host cells into which the nucleic acid construct has been introduced are also encompassed by the invention.

9 Claims, 6 Drawing Sheets

OTHER PUBLICATIONS

Thornberry, N.A. et al. (1992) "A novel heterodimeric cysteine protease is required for interleukin–1β processing in monocytes" *Nature 356*: 768–774.

Walker, N.P.C. et al. (1994) "Crystal Structure of the Cysteine Protease Interleukin–1β–Converting Enzyme: A (p20/p10)$_2$ Homodimer" *Cell 78*: 343–352.

Wang, L. et al. (1994) "Ich–1, an Ice/ced–3–Related Gene, Encodes Both Positive and Negative Regulators of Programmed Cell Death" *Cell 78*: 739–750.

Wilson, K.P. et al. (1994) "Structure and mechanism of interleukin–1β converting enzyme" *Nature 370*: 270–275.

Yuan, J. et al. (1993) "The C. elegans Cell Death Gene ced–3 Encodes a Protein Similar to Mammalian Interleukin–1β–Converting Enzyme" *Cell 75*: 641–652.

TRANSGENIC KNOCKOUT MOUSE HAVING FUNCTIONALLY DISRUPTED INTERLEUKIN-1β CONVERTING ENZYME GENE

This application is a continuation of application Ser. No. 08/323,490, filed on Oct. 14, 1994, now abandoned, entitled: Transgenic Nonhuman Animal Having Functionally Disrupted Interleukin-1β Converting Enzyme. The contents of the aforementioned application is expressly incorporated by reference.

BACKGROUND OF THE INVENTION

Interleukin-1 is a cytokine having a broad spectrum of biological activities (for reviews, see e.g., Dinarello, C. A. and Wolff, S. M. (1993) *New Engl. J. Med.* 328:106–113; and Dinarello, C. A. (1993) *Trends in Pharmacol. Sci.* 14:155–159). IL-1 consists of two structurally related polypeptides, interleukin-1α (IL-1α) and interleukin-1β (IL-1β). The two forms of IL-1 are encoded by different genes and have only 27–33% amino acid identity but they interact with the same receptor and have similar activities. Included among the biological functions attributed to IL-1 are induction of fever, sleep, anorexia and hypotension. IL-1 is also involved in the pathophysiology of inflammatory and autoimmune diseases, including rheumatoid arthritis, septic shock, inflammatory bowel disease and insulin dependent diabetes mellitus. IL-1α has been specifically implicated in the pathophysiology of psoriasis. IL-1 is also thought to play a role in immune responses to infectious agents and in the pathogenesis of myeloid leukemias.

IL-1α and IL-1β are both synthesized as approximately 31 kDa precursor molecules that are subsequently processed to a mature form of approximately 17 kDa. IL-1α and IL-1β differ in that the precursor form of IL-1α (preIL-IL-1α) is biologically active and most of the mature IL-1α (matIL-1α) remains cell-associated, whereas the precursor form of IL-1β (preIL-1β) must be cleaved to its mature form to become active and the mature form of IL-1β (matIL-1β) is secreted from the cell. Only certain cell types process preIL-1β and secrete matIL-1β. Monocytes and macrophages are the most efficient producers and secretors of IL-1β, which is the most abundant form of IL-1 produced upon activation of these cell types.

An intracellular enzyme that cleaves preIL-1β to matIL-1β has been identified and termed interleukin-1β converting enzyme (ICE) (Thornberry et al. (1992) *Nature* 356:768–774; Ceretti, D. P. et al. (1992) *Science* 256:97–100). ICE is a cysteine protease that cleaves the inactive form of IL-1β between residues Asp$^{116}$ and Ala$^{117}$ to release the active 17 kDa form. ICE has not previously been implicated in the processing or secretion of IL-1α. Moreover, since other proteases, such as elastase and cathepsin G, can cleave preIL-1β in vitro to yield matIL-1β (see e.g., Black, R. A. et al. (1988) *J. Biol. Chem.* 263:9437–9442; and Hazuda, D. J. et al. (1990) *J. Biol. Chem*, 265:6318–6322), it is not known whether ICE is the primary or exclusive protease responsible for generation of bioactive IL-1β in vivo.

In addition to cleaving IL-1β, there is evidence that ICE may be involved in apoptosis or programmed cell death. First, overexpression of ICE in a rat fibroblast cell line caused apoptosis. This apoptosis could be blocked either by the product of the bcl-2 gene, a mammalian oncogene that can prevent programmed cell death, or by the product of the cowpox virus crmA gene, which encodes a specific inhibitor of ICE (Yuan, J. et al. (1993) *Cell* 75:641–652; Ray, C. A. et al. (1992) *Cell* 69:597–604; Miura, M. et al. (1993) *Cell* 75:653–660). Moreover, microinjection of the ICE inhibitor crmA into chicken dorsal root ganglion neurons prevented cell death induced by nerve growth factor deprivation (Gagliardini, V. et al. (1994) *Science* 263:826). These observations suggest that ICE may have more widespread biological functions than simply cleaving preIL-1β to matIL-β. This further suggests that an ICE gene mutation could have seriously deleterious effects that would prevent normal biological development and viability.

Because of the apparently harmful role of IL-1 in many disease conditions, therapeutic strategies aimed at reducing the production or action of IL-1 have been proposed. One approach by which to inhibit matIL-1β production and secretion is to block the activity of ICE with a specific ICE inhibitor. To identify ICE inhibitors and evaluate their efficacy, standard control animals and cells against which the activity of ICE inhibitors can be assessed are needed. Additionally, there is a need for model systems in which inhibitors of human ICE can be screened, either in vitro or in vivo. Moreover, while IL-1 has been implicated in the pathology of a number of diseases, the scope of disease conditions in which IL-1 is involved is not fully determined. Accordingly, model systems in which to assess the involvement of IL-1α and/or β in disease states are needed to thereby identify disease conditions which may be treatable by ICE inhibitors.

SUMMARY OF THE INVENTION

This invention pertains to nonhuman animals with somatic and germ cells having a functional disruption of at least one, and more preferably both, alleles of an endogenous interleukin-1β converting enzyme (ICE) gene. Accordingly, the invention provides viable animals having a mutated ICE gene, and thus lacking ICE activity. These animals produce substantially reduced amounts of mature interleukin-1β (matIL-1β) in response to stimuli that produce normal amounts of matIL-1β in wild type control animals. The animals are further characterized by a marked, and unexpected, reduction in mature interleukin-IL-1α (matIL-1α) secretion in response to stimuli that produce normal amounts of matIL-1α in wild type control animals. Moreover, the animals of the invention exhibit resistance to diseases whose pathology is mediated, at least in part, by IL-1. The animals of the invention are useful, for example, as standard controls by which to evaluate ICE inhibitors, as recipients of a normal human ICE gene to thereby create a model system for screening human ICE inhibitors in vivo, and to identify disease states for treatment with ICE inhibitors.

In the transgenic nonhuman animal of the invention, the ICE gene preferably is disrupted by homologous recombination between the endogenous allele and a mutant ICE gene, or portion thereof, that has been introduced into an embryonic stem cell precursor of the animal. The embryonic stem cell precursor is then allowed to develop, resulting in an animal having a functionally disrupted ICE gene. The animal may have one ICE gene allele functionally disrupted (i.e., the animal may be heterozygous for the mutation), or more preferably, the animal has both ICE gene alleles functionally disrupted (i.e., the animal can be homozygous for the mutation). In one embodiment of the invention, functional disruption of both ICE gene alleles produces animals in which expression of the ICE gene product in cells of the animal is substantially absent relative to non-mutant animals. In another embodiment, the ICE gene alleles can be disrupted such that an altered (i.e., mutant) ICE gene product is produced in cells of the animal. A preferred nonhuman animal of the invention having a functionally disrupted ICE gene is a mouse.

Given the essentially complete inactivation of ICE function in the homozygous animals of the invention and the ~50% inhibition of ICE function in the heterozygous animals of the invention, these animals are useful as positive controls against which to evaluate the effectiveness of ICE inhibitors. For example, a stimulus that normally induces production of matIL-1β can be administered to a wild type animal (i.e., an animal having a non-mutant ICE gene) in the presence of an ICE inhibitor to be tested and production of matIL-1β by the animal can be measured. The matIL-1β response in the wild type animal can then be compared to the matIL-1β response in the heterozygous and homozygous animals of the invention, similarly administered the matIL-1β stimulus, to determine the percent of maximal ICE inhibition of the test inhibitor.

Additionally, the animals of the invention are useful for determining whether a particular disease condition involves the action of matIL-1α and/or matIL-1β and thus can be treated by an ICE inhibitor. For example, an attempt can be made to induce a disease condition in an animal of the invention having a functionally disrupted ICE gene. Subsequently, the susceptibility or resistance of the animal to the disease condition can be determined. A disease condition that is treatable with an ICE inhibitor can be identified based upon resistance of an animal of the invention to the disease condition.

Another aspect of the invention pertains to a transgenic nonhuman animal having a functionally disrupted endogenous ICE gene but which also carries in its genome, and expresses, a transgene encoding a heterologous interleukin-1β converting enzyme (i.e., an ICE from another species). Preferably, the animal is a mouse and the heterologous ICE is a human ICE. An animal of the invention which has been reconstituted with human ICE can be used to identify agents that inhibit human ICE in vivo. For example, a stimulus that induces production of matIL-1β can be administered to the animal in the presence and absence of an agent to be tested and the matIL-1β response in the animal can be measured. An agent that inhibits human ICE in vivo can be identified based upon a decreased matIL-1β response in the presence of the agent compared to the matIL-1β response in the absence of the agent.

Yet another aspect of the invention pertains to a nucleic acid construct for functionally disrupting an ICE gene in a host cell. The nucleic acid construct comprises: a) a non-homologous replacement portion; b) a first homology region located upstream of the nonhomologous replacement portion, the first homology region having a nucleotide sequence with substantial identity to a first ICE gene sequence; and c) a second homology region located downstream of the nonhomologous replacement portion, the second homology region having a nucleotide sequence with substantial identity to a second ICE gene sequence, the second ICE gene sequence having a location downstream of the first ICE gene sequence in a naturally occurring endogenous ICE gene. Additionally, the first and second homology regions are of sufficient length for homologous recombination between the nucleic acid construct and an endogenous ICE gene in a host cell when the nucleic acid molecule is introduced into the host cell.

In a preferred embodiment, the nonhomologous replacement portion comprises a positive selection expression cassette, preferably including a neomycin phosphotransferase gene operatively linked to a regulatory element(s). In another preferred embodiment, the nucleic acid construct also includes a negative selection expression cassette distal to either the upstream or downstream homology regions. A preferred negative selection cassette includes a herpes simplex virus thymidine kinase gene operatively linked to a regulatory element(s).

Another aspect of the invention pertains to recombinant vectors into which the nucleic acid construct of the invention has been incorporated. Yet another aspect of the invention pertains to host cells into which the nucleic acid construct of the invention has been introduced to thereby allow homologous recombination between the nucleic acid construct and an endogenous ICE gene of the host cell, resulting in functional disruption of the endogenous ICE gene. The host cell can be a mammalian cell that normally expresses ICE, such as a human macrophage or monocyte, or a pluripotent cell, such as a mouse embryonic stem cell. Further development of an embryonic stem cell into which the nucleic acid construct has been introduced and homologously recombined with the endogenous ICE gene produces a transgenic nonhuman animal having cells that are descendant from the embryonic stem cell and thus carry the ICE gene disruption in their genome. Animals that carry the ICE gene disruption in their germline can then be selected and bred to produce animals having the ICE gene disruption in all somatic and germ cells. Such mice can then be bred to homozygosity for the ICE gene disruption.

DETAILED DESCRIPTION OF THE INVENTION

Figure 1:
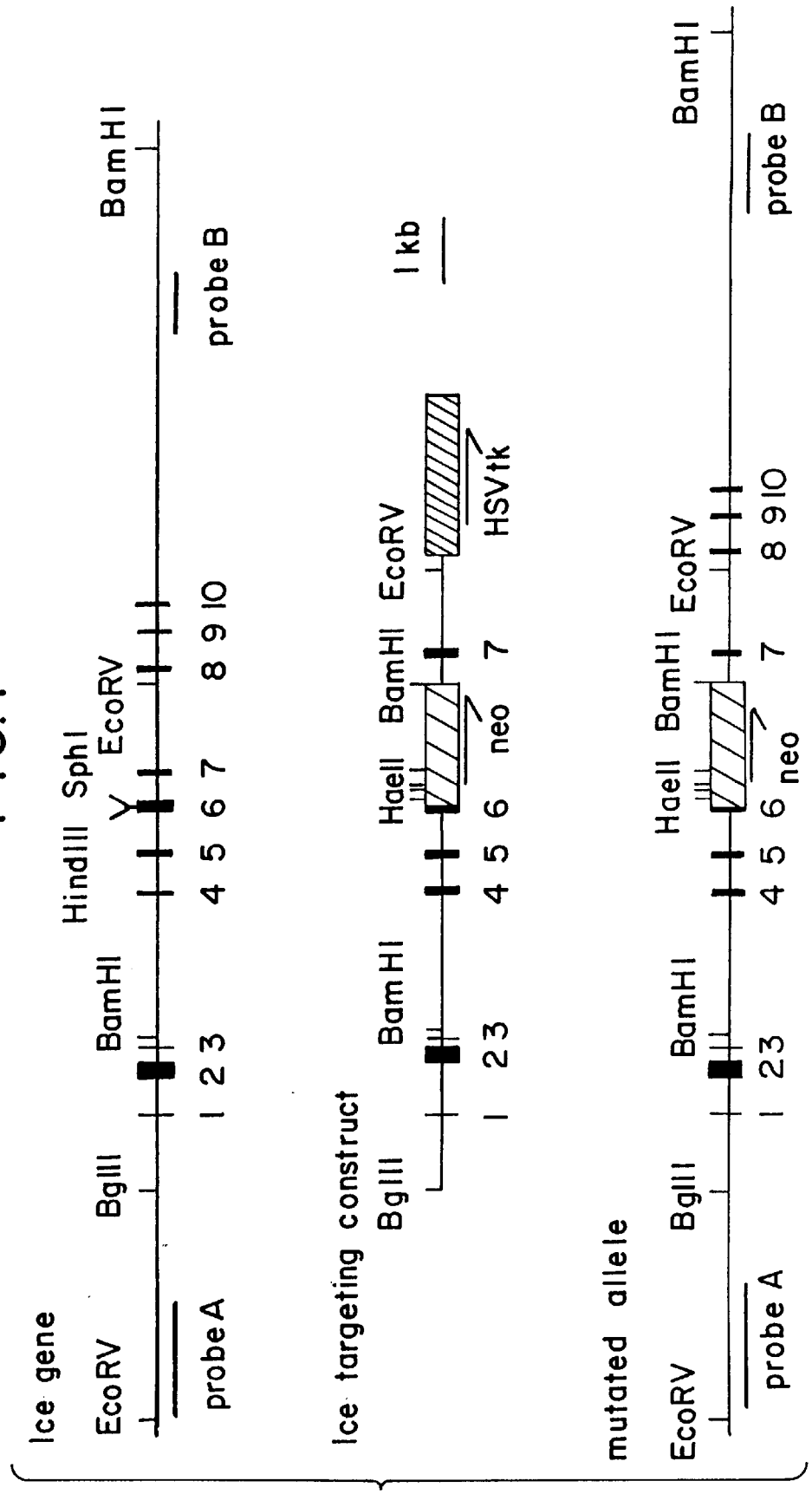
FIG. 1 is a schematic representation of the endogenous murine ICE gene, the ICE targeting construct and the mutated ICE allele produced by homologous recombination between the endogenous ICE gene and the ICE targeting construct.

One aspect of the invention pertains to a nonhuman animal having cells in which at least one allele of an endogenous interleukin-1β converting enzyme (ICE) gene is functionally disrupted. Preferably, both the somatic and germ cells of the animal have an ICE gene allele functionally disrupted. Even more preferably, the somatic and germ cells have both alleles of the ICE gene functionally disrupted. As used herein, a gene that is "functionally disrupted" has a mutation that prevents the normal function of the gene, e.g., prevents expression of a normal ICE gene product or prevents expression of normal amounts of the ICE gene product. The mutation causing the functional disruption can be an insertion, deletion or point mutation(s). In one embodiment, both ICE gene alleles are functionally disrupted such that expression of the ICE gene product is substantially reduced or absent in cells of the animal The term "substantially reduced or absent" is intended to mean that essentially undetectable amounts of normal ICE gene product arc produced in cells of the animal. This type of mutation is also referred to in the art as a "null mutation" and an animal carrying such a null mutation is also referred to as a "knockout animal". In another embodiment, both ICE gene alleles are functionally disrupted such that an altered form of the ICE gene product is expressed in cells of the animal. For example, one or more point mutations or deletion mutations can be introduced into the ICE gene to thereby alter the amino acid sequence of the ICE gene product encoded therein.

In a preferred embodiment, an ICE gene allele is functionally disrupted in a cell by homologous recombination between the allele and a mutant ICE gene, or portion thereof, introduced into the cell. The cell can be a differentiated cell type that normally expresses ICE, such as a macrophage or monocyte, or a macrophage-like or monocyte-like cell line (i.e., cell lines with the properties of these cell types, including the expression of ICE). Alternatively, the cell can be a pluripotent progenitor cell that can develop into an animal, such as an embryonic stem cell. When the cell is an embryonic stem cell, the cell can be introduced into a blastocyst and the blastocyst allowed to develop in a foster animal to thereby produce an animal having somatic and germ cells in which an ICE gene allele is functionally disrupted. Such an animal is referred to herein as a "homologous recombinant" animal. A preferred homologous recombinant animal of the invention is a mouse.

To create a homologous recombinant cell or animal, a targeting vector is prepared which contains DNA encoding an ICE gene, or portion thereof, having a mutation introduced therein. A preferred targeting vector for creating a null mutation in an endogenous ICE gene includes ICE-encoding DNA into which has been inserted non-ICE encoding DNA. For example, in one embodiment, a targeting vector of the invention for functionally disrupting an endogenous ICE gene in a cell comprises:

a) a nonhomologous replacement portion;
 b) a first homology region located upstream of the nonhomologous replacement portion, the first homology region having a nucleotide sequence with substantial identity to a first ICE gene sequence; and
 c) a second homology region located downstream of the nonhomologous replacement portion, the second homology region having a nucleotide sequence with substantial identity to a second ICE gene sequence, the second ICE gene sequence having a location downstream of the first ICE gene sequence in a naturally occurring endogenous ICE gene.

Thus, the nonhomologous replacement portion is flanked 5' and 3' by nucleotide sequences with substantial identity to ICE gene sequences. A nucleotide sequence with "substantial identity" to an ICE gene sequence is intended to describe a nucleotide sequence having sufficient homology to an ICE gene sequence to allow for homologous recombination between the nucleotide sequence and an endogenous ICE gene sequence in a host cell. Typically, the nucleotide sequences of the flanking homology regions are at least 80%, more preferably at least 90%, even more preferably at least 95% and most preferably 100% identical to the nucleotide sequences of the endogenous ICE gene to be targeted for homologous recombination. Most preferably, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous ICE gene in a host cell when the vector is introduced into the host cell. Typically, the flanking homology regions are at least 1 kilobase in length and more preferably are least several kilobases in length.

A typical targeting vector has a positive selection expression cassette as the nonhomologous replacement portion. The term "positive selection expression cassette" refers to nucleotide sequences encoding a positive selection marker operatively linked to regulatory elements that control expression of the positive selection marker (e.g., promoter and polyadenylation sequences). A "positive selection marker" allows for selection of cells which contain the marker, whereas cells that do not contain and express the marker are selected against (e.g., are killed by the selecting agent). For example, a preferred positive selection expression cassette includes a neomycin phosphotransferase ("neo") gene operatively linked to a promoter and a polyadenylation signal. Cells carrying and expressing the neo gene exhibit resistance to the selecting agent G418.

In addition to the positive selection expression cassette, a targeting vector of the invention typically also includes a negative selection expression cassette located distal to either the upstream or downstream homology regions (i.e., the regions substantially identical to ICE-encoding sequences). A "negative selection expression cassette" refers to nucleotide sequences encoding a negative selection marker operatively linked to regulatory elements that control expression of the negative selection marker. A "negative selection marker" allows for selection against cells which carry the marker, e.g., cells that contain and express the marker are killed by a selecting agent, whereas cells that do not contain and express the negative selection marker survive. For example, a preferred negative selection expression cassette includes a herpes simplex virus thymidine kinase ("tk") gene operatively linked to a promoter and a polyadenylation signal. Cells that contain and express the tk gene can be killed, for example, by the selecting agent gancyclovir.

This configuration of the targeting vector allows for use of the "positive/negative" selection technique for selecting homologous recombinants: cells into which the targeting vector has been introduced are selected that contain and express the positive selection marker but which have lost the negative selection marker. Accordingly, these cells carry the nonhomologous replacement portion DNA (e.g., the inserted neo gene) but have lost the DNA encoding the negative selection marker located distal thereto in the targeting vector, likely as a result of homologous recombination between the targeting vector and the endogenous ICE gene.

In a preferred embodiment, the targeting vector includes flanking homology regions having substantial identity to mouse ICE (mICE) gene sequences to thereby target an endogenous mouse ICE gene in a mouse host cell (e.g., a murine embryonic stem cell) for homologous recombination. Murine ICE genomic DNA used as the flanking homology regions of the targeting vector can be isolated from a murine genomic DNA library by screening the library with a cDNA probe encompassing all or part of the murine ICE cDNA using standard techniques. Preferably, a genomic DNA library screened is prepared from cells isogenic with the cell to be transfected with the targeting vector. For example, a genomic library from the 129/Sv strain of mouse (available commercially from Stratagene) can be screened to isolate mouse ICE genomic DNA for use in a targeting vector for transfection into the D3 embryonic stem cell line derived from strain 129/Sv. The nucleotide sequence of the mouse ICE cDNA and predicted amino acid sequence of the mouse ICE protein are disclosed in Nett et al. (1992) *J. Immunol.* 149:3254–3259 and are shown in SEQ ID NOs: 15 and 16, respectively. The structure and complete nucleotide sequence of the murine ICE gene are disclosed in Casano, F. J. et al. (1994) *Genomics* 20:474–481.

The genomic structure and restriction map of the mouse ICE gene is shown in FIG. 1. To create a targeting vector for functionally disrupting an endogenous mouse ICE gene, the nonhomologous replacement portion (e.g., the neo gene) preferably is inserted into exon 6 of the mouse ICE gene in the targeting vector. The nonhomologous replacement portion preferably is flanked upstream by exons 1 through 5 and downstream by exon 7 and portions of the intron between exon 7 and exon 8 of the mouse ICE gene. However, it will be appreciated by the skilled artisan that a nonhomologous replacement portion can be inserted at other locations within the ICE gene, and flanked by different homology regions, to thereby functionally disrupt the gene. Construction of a targeting vector for functional disruption of a mouse ICE gene is described in further detail in Example 1. The functional disruption of the mICE gene sequence may prevent expression of a full-length mICE mRNA transcript (e.g. by insertion of the neo gene) or may lead to expression of an mICE mRNA transcript that encodes an altered form of mICE.

Alternatively, to target a human ICE (hICE) gene in a human host cell (e.g., a macrophage or monocyte) for homologous recombination, the targeting vector includes flanking homology regions having substantial identity to human ICE gene sequences. Human ICE genomic DNA sequences can be isolated by screening a human genomic DNA library with a cDNA probe encompassing all or part of the human ICE cDNA using standard techniques. The nucleotide sequence of the human ICE cDNA and predicted amino acid sequence of the ICE protein are disclosed in Thornberry et al. (1992) *Nature* 356:768–774 and PCT International Publication No. WO 91/15577 and are shown in SEQ ID NOs: 17 and 18, respectively. As described for the mouse ICE gene, the functional disruption of the human ICE gene sequence in a human cell may prevent expression of a full-length hICE mRNA transcript or may lead to expression of an hICE mRNA transcript that encodes an altered form of hICE.

To functionally disrupt an endogenous ICE gene allele in a host cell, a targeting vector of the invention is introduced into the host cell, e.g., a differentiated cell that normally expresses ICE or an embryonic stem cell, and homologous recombinants are selected. A targeting vector can be introduced into a host cell by any of several techniques known in the art suitable for the introduction of exogenous DNA (e.g., calcium phosphate precipitation, DEAE-dextran transfection, microinjection, lipofection and the like) but is most preferably introduced into the host cell by electroporation. After introduction of the vector into the host cell, the cell is cultured for a period of time and under conditions sufficient to allow for homologous recombination between the introduced targeting vector and an endogenous ICE gene. Host cells are selected (e.g., by the positive/negative selection techniques described above) and screened for homologous recombination at the endogenous ICE gene locus by standard techniques (e.g., Southern hybridizations using a probe which distinguishes the normal endogenous allele from the homologous recombinant allele).

To create a cell (e.g., macrophage or a monocyte) homozygous for the ICE gene disruption, the G418 escalation method of Mortensen, R. N. et al. ((1992) *Mol. Cell. Biol.* 12:2391–2395) can be used on the heterozygous cells. Alternatively, the first allele of a wild type host cell can be disrupted by a first homologous recombination event that is selected with one marker (e.g., G418 resistance) and then the second allele of the heterozygous cells can be disrupted by a second homologous recombination event that is selected with a different marker (e.g., hygromycin resistance) (see e.g., TERiele, H. (1990) *Nature* 348:649–651).

To create a homologous recombinant animal of the invention, an embryonic stem cell having one ICE gene allele functionally disrupted is introduced into a blastocyst, the blastocyst is implanted into a pseudopregnant foster mother, and the embryo allowed to develop to term. The resultant animal is a chimera having cells descendant from the embryonic stem cell. Chimeric animals in which the embryonic stem cell has contributed to the germ cells of the animal can be mated with wild type animals to thereby produce animals heterozygous for the ICE gene disruption in all somatic and germ cells. The heterozygous animals can then be mated to create animals homozygous for the ICE gene disruption (i.e., having both ICE gene alleles functionally disrupted). These animals can be used as control or test animals for in vivo screening assays (described in further detail below). Additionally, cells of the animal homozygous for the ICE gene disruption can be isolated from the animals and cultured for use in in vitro screening assays. For example, peritoneal exudate macrophages (e.g., thioglycolate-elicited), which normally express ICE, can be isolated from the animals by standard techniques. Furthermore, immortalized cell lines can be prepared from cells of the animal using standard techniques for cell immortalization, e.g., by transfection of the cells with an expression vector encoding myc, ras or SV40 large T antigen.

Targeting vectors and methodologies for functionally disrupting a murine ICE gene by homologous reconbination are described in further detail in Examples 1–3. For additional descriptions of targeting vectors and methodologies, see also e.g., Thomas, K. R. et al. (1986) *Cell* 44:419–428; Thomas, K. R. et al. (1987) *Cell* 51:503–512; Thomas, K. R. et al. (1992) *Mol. Cell. Biol.* 12:2919–2923; Deng, C. and Capecchi, M. R. (1992) *Mol. Cell. Biol.* 12:3365–3371; Hasty, P. et al. (1992) *Mol. Cell. Biol.* 12:2464–2474; Li, E. et al. (1992) *Cell* 69:915; Zhang, H., et al. (1994) *Mol. Cell.*

*Biol.* 14:2404–2410; Bradley, A. in *Teratocarcinomas and Embryonic Stem Cells. A Practical Approach*, E. J. Robertson, ed. (IRL, Oxford, 1987) pp. 113–152; PCT International Publication No. WO 90/11354; PCT International Publication No. WO 91/01140; PCT International Publication No. WO 91/19796; PCT International Publication No. WO 92/20808; and PCT International Publication No. WO 93/04169. Both copies of an ICE gene can be functionally disrupted according to the methods described in PCT International Publication WO 93/16177. Additionally, a recombinase can be used to functionally disrupt an ICE gene by homologous recombination as described in PCT International Publication WO 93/22443.

In addition to allowing for introduction of a null mutation in an ICE gene allele, similar techniques can be used to introduce point mutations or deletions into an ICE gene allele. For example, a point mutation(s) can be introduced into exon 6 of the mouse ICE gene at the codon encoding the active site cysteine of ICE, alone or in conjunction with one or more point mutations introduced into codons encoding the amino acid residues of the active site. For example, the active site cysteine of murine ICE (at amino acid position 284) or of human ICE (at amino acid position 285) can be mutated to abrogate ICE protease activity or to alter its substrate specificity. Additionally, one or more of the four amino acid residues comprising the P1 carboxylate binding pocket can be mutated. In human ICE, the amino acid residues of the active site pocket are $Arg^{179}$, $Gln^{283}$, $Arg^{341}$ and $Ser^{347}$ (see the description of the crystal structure of human ICE disclosed in Walker, N. P. C. et a. (1994) *Cell* 78:343–352) and these residues are conserved in murine ICE. Point or deletion mutations can be introduced into an ICE gene allele by, for example, the "hit and run" homologous recombination procedure (as described in Valancius, V. and Smithies, O. (1991) *Mol. Cell. Biol.* 11:1402–1408: and Hasty, P. et al. (1991) *Nature* 350:243–246) or by the double replacement homologous recombination procedure (as described in Wu, H. et al. (1994) *Proc. Natl. Acad. Sci. USA* 91:2819–2823). Accordingly, in another embodiment, the invention provides homologous recombinant cells and animals (e.g., human cells or nonhuman animals) that express an altered ICE gene product.

As described in further detail in the Example 4, secretion of mature interleukin-1β (matIL-1β) by cells of homologous recombinant animals homozygous for a null mutation of the ICE gene is substantially reduced relative to a non-mutant wild-type control animal (i.e., an animal of the same species in which the ICE gene alleles are not functionally disrupted). With regard to matIL-1β production, the term "substantially reduced" is intended to mean that the amount of matIL-1β produced by the homozygous cells or animals of the invention, is at least 50%, more preferably 75% and even more preferably greater than 90% less than that produced by non-mutant wild-type animals of the same species. In a preferred embodiment, the levels of matIL-1β produced by the cells or animals is essentially undetectable by standard techniques, such as a commercially available enzyme linked immunosorbent assay. Animals heterozygous for the ICE gene disruption exhibit approximately half the level of matIL-1β as the homozygous animals. For example, when matIL-1β production is essentially undetectable in homozygous animals relative to wild type animals (i.e., ~100% reduced), the matIL-1β levels in the heterozygous animals is ~50% reduced from wild type levels.

Furthermore, in animals homozygous for the ICE gene disruption, secretion of mature interleukin-1α (matIL-1α) is unexpectedly, and substantially, reduced relative to non-mutant wild-type control animals. With regard to IL-1α secretion, the term "substantially reduced" is intended to mean that the amount of matIL-1α secreted in the homozygous mutant animal, or by cells derived from the animal, is at least 25% less, more preferably at least 50% less. and even more preferably at least 75% less, than the amount of matIL-1α secreted in a non-mutant control animal of the same species. Previous studies had not suggested a role for ICE in the secretion of matIL-1α; the results described herein indicate that ICE and/or matIL-1β, produced by cleavage of preIL-1β by ICE, is necessary for production and/or release of normal amounts of IL-1α. Accordingly, the cells and animals of the invention are unexpectedly applicable to the study of the effects of matIL-1α as well as matIL-1β.

The features and characteristics of the animals of the invention, and cells derived therefrom, make them useful for a wide variety of applications, as described in further detail in the subsections below:

Uses of the Animals and Cells of the Invention

Figure 5:
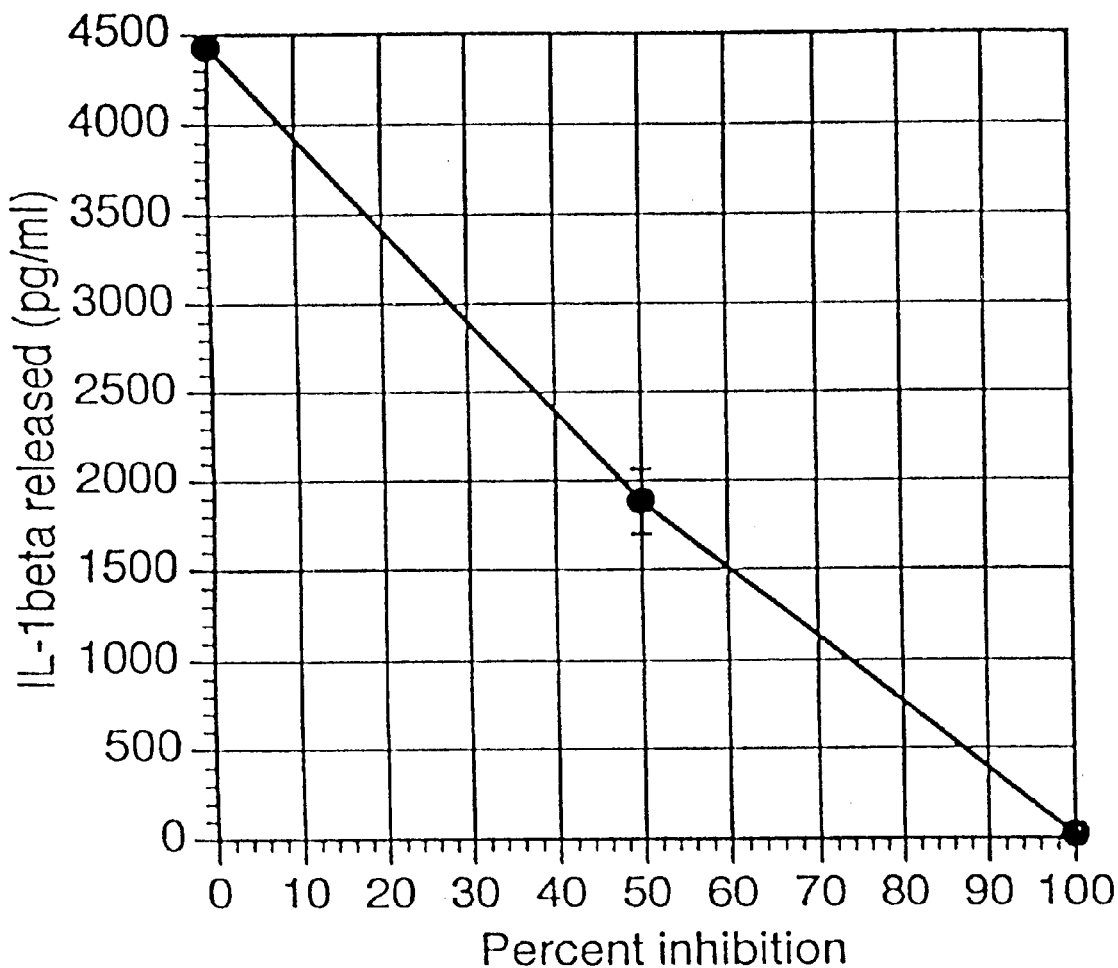
FIG. 5 is a graph of a standard curve of the amount of matIL-1β release in ICE +/+, mice (representing 0% ICE inhibition), ICE +/– mice (representing 50% ICE inhibition) and ICE –/– mice (representing 100% ICE inhibition).

1. In one embodiment, the animals of the invention, or cells derived therefrom, are used as positive control animals by which to evaluate the efficacy of ICE inhibitors. Prior to the current invention, there was no positive standard against which ICE inhibitors could be assessed in screening assays. The homozygous and heterozygous animals of the invention provide such standards. In a screening assay to identify and assess the efficacy of ICE inhibitors, a wild type animal (or cells derived therefrom) not treated with the inhibitor is used as the 0% inhibition standard, an animal heterozygous for an ICE gene disruption (or cells derived therefrom) is used as the 50% inhibition standard and an animal homozygous for an ICE gene disruption (or cells derived therefrom) is used as the 100% inhibition standard. The amount of ICE activity in a subject treated with an ICE inhibitor is then assessed relative to these standards. The use of the animals of the invention, or cells derived therefrom, as positive controls by which to standardize the efficacy of an ICE inhibitor, such as the ICE inhibitor Ac-YVAD-CHO, a tetrapeptide aldehyde, is described in further detail in Example 4 and FIG. 5.

2. The animals of the invention, or cells derived therefrom, also can be used to screen ICE inhibitors for side effects or toxicity resulting from the inhibitor's action on a target(s) other than ICE itself (e.g., an ICE isoforms). For example, an ICE inhibitor is administered to an animal of the invention homozygous for an ICE null mutation and the resulting effects are monitored to evaluate side effects or toxicity of the inhibitor. Since the animal lacks the normal target of the ICE inhibitor (i.e., active ICE protein), an effect observed upon administration of the inhibitor to the ICE null mutant can be attributed to a side effect of the ICE inhibitor on another target(s) (e.g., an ICE isoform). Accordingly, the animals of the invention are useful for distinguishing these side effects from the direct effects of the inhibitor on ICE activity.

3. The animals of the invention can also be used in in vivo screening assays to identify diseases in which matIL-1α and/or matIL-1β play a role in the pathogenesis of the diseases. Such screening assays are further useful for identifying diseases that may be treated by ICE inhibitors. Since the animals of the invention have not only significantly reduced levels of matIL-1β but also secrete substantially reduced amounts of matIL-1α, these animals are unexpectedly applicable to evaluating the role of IL-1α in particular disease conditions (e.g., psoriasis).

To identify a disease condition involving matIL-1α and/or matIL-1β secretion, and thus treatable by an ICE inhibitor, an attempt is made to induce the disease condition in an animal of the invention homozygous for the ICE gene disruption. In one embodiment, the attempt to induce the disease condition involves administering a stimulus to the animal that induces the disease condition in a wild-type animal (e.g., induction of septic shock by administration of lipopolysaccharide (LPS)). In another embodiment, the attempt to induce the disease condition involves breeding an animal of the invention with another animal genetically prone to a particular disease. The animals are crossbred at least until they are homozygous for the ICE null mutation. For example, an animal of the invention can be bred with an animal prone to a particular autoimmune disease to assess the involvement of IL-1 in the pathology of the autoimmune disease and to determine whether an ICE inhibitor may be effective in treating the autoimmune disease. Examples of mice strains genetically susceptible to particular autoimmune diseases include the MRL/lpr mouse (Cohen, P. L. et al. (1991) *Ann. Rev. Immunol.* 9:243–269), which is a model for lupus erythematosus, and the NOD mouse (Rossinni, A. A. (1985) *Ann. Rev. Immunol.* 3:289–320), which is a model for insulin-dependent diabetes mellitus. Non-limiting examples of other mouse strains (and their disease susceptibilities) which can be bred with the animals of the invention include: DBA/1 (collagen-induced arthritis; model for rheumatoid arthritis)(Wooley, P. H. et al. (1981) *J. Exp. Med.* 154:688–700), BALB/c (proteoglycan-induced arthritis and spondylitis; model for rheumatoid arthritis and ankylosing spondylitis)(Glant, T. T. et al. (1987) *Arthritis Rheum.* 30:201–212), PL/J (experimental autoimmune encephalomyclitis; model for multiple sclerosis)(Fritz, R. B. et al. (1983) *J. Immunol.* 130:191–194), NZB/KN (polyarthritis; model for rheumatoid arthritis and osteoarthritis)(Nakamura, K. et al. (1991) *Arthritis Rheum.* 34:171–179), C57BL (osteoarthritis; Pataki, A. et al. (1990) *Agents Actions* 29:201–209), STR/ORT (polyarthritis; model for rheumatoid arthritis and osteoarthritis)(Dunham, J. et al. (1990) *J. Orthop. Res.* 8:101–104), and Tsk/+ (systemic sclerosis; Siracusa, L. D. et al. (1993) *Genomics* 17:748–751). For MHC-associated disease models, offspring of the crossbreeding are selected that maintain the disease-susceptible MHC haplotype. Many mouse strains genetically susceptible to particular diseases are available from The Jackson Laboratory, Bar Harbor, Me. or other commercial or academic sources. The disease condition is then induced in the crossbred animals either spontaneously or experimentally.

Following induction of the disease condition in the ICE null mutant animal, the susceptibility or resistance of the animal to the disease condition is determined. Resistance of the animal to the disease condition, relative to a wild-type control animal, is indicative that the pathology of the disease condition involves the action of matIL-1α and/or matIL-1β and thus that the disease condition is treatable with an ICE inhibitor. As an exemplification of this utility, Example 6 demonstrates that homozygous ICE null mutant mice are resistant to LPS-induced septic shock, a disease in which IL-1 has previously been implicated to be involved in the pathology. Thus, using a disease model believed to involve the action of IL-1, the resistance of homozygous ICE null mutants to the disease was demonstrated.

The animals of the invention can also be used to determine whether the pathophysiology of a particular disease condition involves either matIL-1α or matIL-1β. The expression of either matIL-1α or matIL-1β (both of which are reduced in ICE −/− animals) can be restored in ICE −/− animals by introducing a transgene encoding the mature form of either one or the other cytokine into the genome of the ICE −/− animals by standard techniques. For example, a nucleic acid construct encoding the mature form of IL-1α or β, operatively linked to appropriate regulatory elements, can be injected into a fertilized oocyte obtained from an ICE −/− animal. In this manner, ICE −/− animals that express predominantly either matIL-1α or matIL-1β can be created. Disease conditions can then be induced in these animals to assess the specific role of either IL-1α or β in the pathophysiology of the disease.

4. In another embodiment, an animal of the invention homozygous for an ICE null mutation, or a cell derived therefrom, is reconstituted with a human ICE gene to create a nonhuman cell or animal that expresses a human ICE gene product. These cells and animals can then be used to screen compounds to identify agents that inhibit the activity of human ICE, either in cultured cells or in vivo in animals. A human ICE reconstituted animal can be made by introducing nucleic acid encoding human ICE into the genome of embryonic progenitor cells obtained from an animal of the invention and allowing the embryonic cells to develop using standard techniques for creating transgenic and homologous recombinant animals. Nucleic acid encoding human ICE can be integrated randomly into the genome of an ICE deficient animal (e.g., by microinjection of a human ICE gene construct into fertilized oocytes obtained from an ICE deficient animal) or the nucleic acid can be integrated by homologous recombination into the endogenous ICE locus (i.e., the endogenous ICE gene bearing the null mutation can be replaced by an exogenously introduced human ICE gene). The human ICE gene construct can include upstream and/or downstream regulatory elements that allow for either tissue-specific, regulated expression of the ICE polypeptide or constitutive expression of the human ICE polypeptide in cells of the mammal. A human ICE-reconstituted animal of the invention also provides a source of nonhuman cells that express human ICE polypeptide. Such cells (e.g., macrophages or monocytes) can be isolated from the animal and, if necessary, immortalized by standard techniques.

A nonhuman animal of the invention having cells expressing human ICE polypeptide can be used to screen agents to identify compounds that can inhibit human ICE function in vivo. For example, a panel of compounds can be administered individually to the animal (e.g., mouse) together with a stimulus that normally induces production of matIL-1β. Non-limiting examples of stimuli that can be used to induce matIL-1β production include lipopolysaccharide (LPS), either alone or together with adenosine triphosphate (ATP), zymosan and carrageenan. Production of matIL-1β can then be assessed in the presence and absence of the test compound. Production of matIL-1β in the animal can be assessed directly or indirectly. Preferably, matIL-1β production is measured directly by determining the amount of matIL-1β protein in at least one biological fluid of the animal. For example, matIL-1β levels can be measured in the sera, plasma or peritoneal fluid of the animals or in air pouch washes or tissue chamber exudates from the animal. Alternatively, matIL-1β production can be measured indirectly by measuring matIL-1β -associated symptoms in the animal (e.g., lethargy, shaking, piloerection, etc.) Methods for evaluating matIL-1β production in animals (e.g., LPS-treated animals) is described in further detail in Example 6.

When the human ICE-reconstituted animals are used to screen ICE inhibitors, reduced matIL-1β production in the presence of a test agent is used as an indicator that the agent inhibits the activity of human ICE in vivo. Alternatively, the effect of the compounds on matIL-1β production can be screened in vitro by incubating the test compounds with cells obtained from the human ICE-reconstituted animal together with a stimulus that normally induces production of matIL-1β and measuring the resultant amount of matIL-1β produced.

5. The animals of the invention, or cells derived therefrom, can be used to identify and/or clone ICE homologues or isoforms in the absence of the normal ICE background. Northern hybridization analyses of the homozygous knockout animals of the invention revealed at least one band that weakly hybridized to an ICE probe (see FIG. 2, described in Example 3), suggesting that mRNA(s) having sequences related to the ICE gene are still expressed in the animal (although these sequences do not compensate for the disrupted ICE gene in producing matIL-1β). Accordingly, a cDNA library prepared from mRNA isolated from cells of a homozygous animal of the invention can be screened with an ICE cDNA probe to isolate cDNAs related in sequence to the disrupted ICE gene 6. The animals of the invention can also used to create additional animals having multiple mutations. In one embodiment, an animal of the invention is bred with an animal carrying another null mutation(s) to create double (or triple, etc.) knockout animals. In another embodiment, an animal of the invention is used to create an embryonic stem cell line into which targeting vectors for functional disruption of additional genes can be introduced. In such a manner, animals having multiple ICE/ICE homologue deficiencies can be created. For example, a gene encoding an ICE homologue (e.g., identified according to section 5, above or by other molecular biological methods) can be functionally disrupted and an animal carrying the disrupted ICE homologue gene can be bred with an animal of the invention carrying a disrupted ICE gene, to thereby creating a double ICE/ICE homologue knockout animal. These multiple ICE deficient animals can be used to assess the efficacy of ICE inhibitors on remaining ICE homologues in the animal. Moreover, the role of remaining ICE homologues in the multiple ICE deficient animals in disease states can be assessed.

The ICE knockout animals also can be bred with other knockout or transgenic animals to examine the role of the deficient gene products in various disease conditions. Non-limiting examples of knockout and transgenic animals known in the art (and their disease susceptibilities) which can be bred with the animals of the invention to examine disease states include: interleukin-2 (IL-2) knockout (inflammatory bowel disease)(Sadlack, B. et al. (1993) *Cell* 75:253–261), T cell receptor knockouts (inflammatory bowel disease)(Mombaerts, P. et al. (1993) *Cell* 75:275–282), Major Histocompatibility Complex (MHC) Class II knockout (inflammatory bowel disease) (Mombaerts, P. et al. (1993) *Cell* 75:275–282), interleukin 10 (IL-10) knockout (inflammatory bowel disease)(Kuhn, R. et al. (1993) *Cell* 75:263–274), TGFβ1 knockout (multi-organ inflammation)(Shull, M. M. et al. (1992) *Nature* 359:693–699), TNFα transgenic (arthritis) (Keffer, J. et al. (1991) *EMBO J*. 10:4025–4031) and TNFα transgenic-T cell specific (systemic toxicity of TNFα) (Probert, L. et al. (1993) *J. Immunol.* 151:1894–1906). A disease condition can be induced spontaneously or experimentally in the double (triple, etc.) knockout or transgenic animals to assess the involvement of the affected gene products in the disease.

7. The animals of the invention are also useful to determine whether a particular substance is a substrate for ICE. ICE is a cysteine protease that cleaves proIL-1β to matIL-1β, but may also be Involved in the proteolysis of other endogenous substrates. To assess whether a precursor form of a putative substrate is cleaved to a mature form by ICE, the presence or absence of the mature form of the putative substrate in the ICE deficient animals is determined. A mature form of a putative substrate that is a cleavage product of ICE will be subtantially reduced or absent in the ICE deficient animals of the invention.

8. The animals of the invention can also be used as recipients of tissues transplanted from congenic wild-type animals to identify a tissue(s) that expresses an ICE homologue or ICE isoform having a detectable activity. The ICE homologue or isoform so identified can be isolated from the tissue and/or cloned by standard molecular biology techniques.

This invention is further illustrated by the following examples which should not be construed as limiting. The contents of all references and published patents and patent applications cited throughout the application are hereby incorporated by reference.

EXAMPLE 1

Construction of ICE Gene Targeting Vector

A partial murine ICE cDNA clone was isolated from a mouse macrophage cDNA library (obtained commercially from Stratagene) using a full length human ICE coding sequence (kindly provided by Dr. T. Ghayur) as a probe by standard techniques. The murine ICE cDNA fragment was then used as a probe to screen a genomic DNA library made from the 129/Sv strain of mouse (obtained commercially from Stratagene; and an additional library provided by Dr. R. Jacnisch), again using standard techniques. The isolated murine ICE genomic clones were then subcloned into a plasmid vector, pBluescript (obtained commercially from Stratagene), for restriction mapping, partial DNA sequencing, and construction of the targeting vector. The murine ICE gene is composed of 10 exons, with the active site cysteine characteristic of cysteine proteases encoded within exon 6. To functionally disrupt the ICE gene, a targeting vector was prepared in which non-homologous DNA was inserted within exon 6, deleting 31 bp of ICE coding sequence in the process and rendering the remaining downstream ICE coding sequences out of frame with respect to the start of translation. Therefore, if any translation products were to be formed from alternately spliced transcripts of the ICE gene, they would not contain the active site cysteine residue.

The ICE targeting vector was constructed using the plasmid pPNT (kindly provided by Dr. R. Mulligan). This plasmid carries the neomycin phosphotransferase (neo) gene under the control of the phosphoglycerokinase promoter and the herpes simplex thymidine kinase (HSV tk) gene under the control of the same promoter. A 2.2 kb SphI-NotI ICE fragment containing part of exon 6 and sequences downstream was isolated from a genomic clone and subcloned into pBluescript at the BamHI and NotI site using a SphI-BamHI adapter made with two oligonucleotides with the following sequences: 5' GATCCGAACCCCTTCGCATG 3' (SEQ ID NO: 1) and 5' CGAAGGGGTTCG 3' (SEQ ID NO: 2). The 2.2 kb ICE fragment was then isolated as a BamHI-NotI fragment and the NotI end was filled in with Klenow. This fragment was inserted into pPNT at the BamHII and EcoRI sites after filling in the EcoRI site, thus positioning the fragment right after the neo gene on the 5' end and right before the thymidine kinase gene at the 3' end. This plasmid is referred to as pPNT3'ICE. A 6.5 kb BglII and HindIII fragment containing ICE upstream sequences as well as Exon 1 through 5 and ending in the middle of Exon 6 was subcloned into pBluescript and subsequently excised out as a NotI-XhoI fragment and inserted 5' of the neo gene in the pPNT3'ICE vector. In this final targeting construct, a 31 bp ICE sequence contained within the HindIII and the SphI sites was deleted from Exon 6.

The ICE gene targeting vector is diagrammed schematically in FIG. 1. The positive selection neo gene is located within exon 6 of the ICE sequences and in the same orientation as the ICE gene, whereas the negative selection HSV tk gene is at the 3' end of the construct. This configuration allowed for the use of the positive and negative selection approach for homologous recombination (Mansour, S. L. et al. (1988) *Nature* 336:348). Prior to transfection into embryonal stem cells, the plasmid was linearized by NotI digestion.

EXAMPLE 2

Transfection and Analysis of Embryonal Stem Cells

D3 embryonal stem cells (Doestschman, T. C. et al. (1985) *J. Embryol. Exp. Morphol.* 87:27–45) were cultured on a neomycin resistant embryonal fibroblast feeder layer grown in Dulbecco's Modified Eagles medium supplemented with 15% Fetal Calf Serum, 2 mM glutamine, penicillin (50 u/ml)/streptomycin (50 µg/ml), non-essential amino acids, 100 µM 2-mercaptoethanol and 500 u/ml leukemia inhibitory factor. Medium was changed daily and D3 cells were subcultured every three days. $8 \times 10^6$ D3 cells were transfected with 25 µg of linearized plasmid by electroporation (25 µF capacitance and 400 Volts). The transfected cells were cultured for the first 5 days in $2 \times 10^{-6}$ M gancyclovir and 300 µg/ml neomycin and for the last 3 days in neomycin alone.

After expanding the clones, an aliquot of cells was frozen in liquid nitrogen. DNA was prepared from the remainder of cells for genomic DNA analysis to identify clones in which homologous recombination had occurred between the endogenous ICE gene and the targeting construct. To prepare genomic DNA, ES cell clones were lysed in 100 mM Tris-HCl, pH 8.5, 5 mM EDTA, 0.2% SDS, 200 mM NaCl and 100 µg of proteinase K/ml. DNA was recovered by isopropanol precipitation, solubilized in 10 mM Tris-HCl, pH 8.0/0.1 mM EDTA.

To identify homologous recombinant clones, genomic DNA isolated from the clones was digested either with EcoRV and HaeII or with BamHI. After restriction digestion, the DNA was resolved on a 0.8% agarose gel, blotted onto a Hybond-N membrane and hybridized at 65° C. with probe A (for the EcoRV-Hae II digest) or probe B (for the BamHI digest). Probe A is a 2.2 kb EcoRV/XhoI fragment that binds a region of the ICE gene proximal to the 5' end of the targeting vector. Probe B is a 1.2 kb XmnI/NcoI fragment that binds a region of the ICE gene distal to the 3' end of the targeting vector. The locations of the two probes within the mouse ICE gene are illustrated in FIG. 1. After standard hybridization, the blots were washed with 40 mM $NaPO_4$ (pH 7.2), 1 mM EDTA and 1% SDS at 65° C. and exposed to X-ray film. Hybridization of probe A to the wild type ICE allele digested with EcoRV-HaeII resulted in a fragment of approximately 13 kb, whereas hybridization of probe A to the mutant ICE allele having the neo insertion within exon 6 resulted in a fragment of approximately 12 kb. These two fragments were readily discernible by autoradiography of the hybridization blots. For the BamHI digest, hybridization of probe B to the wild type ICE allele resulted in a fragment of approximately 15 kb, whereas hybridization of probe B to the mutant ICE allele resulted in a fragment of approximately 11 kb. These two fragments were also readily discernible by autoradiography.

Of three ES cell transfection experiments performed and analyzed, yielding a total of 600 neo resistant clones, only one clone (#164) was identified that had undergone homologous recombination between the endogenous ICE gene and the targeting vector.

EXAMPLE 3

Generation of ICE Deficient Mice

C57BL/6 female and male mice were mated and blastocysts were isolated at 3.5 days of gestation. 10–12 cells from Clone 164 (described in Example 2) were injected per blastocyst and 7–8 blastocysts were implanted in the uterus of a pseudopregnant B6D2F1 female. Pups were delivered by cesarean section on the 18 th day of gestation and placed with a foster BALB/c mother. Ten male and one female chimeras exhibiting more than 70% agouti patches (indicating cells decendent from clone 164) were born. Male and female chimeras were mated with female and male C57BL/6 mice, respectively, and germline transmission was determined by the agouti coat color. All eleven chimeras were able to transmit the ICE gene mutation through the germline. As would be predicted from Mendelian genetics, 50% (86/173) of the offspring with agouti coat color derived from mating chimeras with C57BL/6 mice were heterozygous for the ICE null mutation. These heterozygous animals were mated and, again as would be predicted from Mendelian genetics, approximately 25% of the offspring were homozygous for the ICE null mutation. Genotyping of the animals was accomplished by obtaining tail genomic DNA, digesting with EcoRV and either HaeII or BamHI and hybridizing with either probe A or B, as described for the ES cells in Example 2.

The average litter size was 6 animals and there was equal representation of both sexes in the homozygous animals. The ICE −/− mice developed normally, appeared healthy and were capable of reproducing with average litter sizes of 6. Therefore, the null mutation in the ICE gene did not have any adverse effects on embryogenesis or early development. No overt abnormalities were discernible in the adult animals. Moreover, histopathological evaluation of all major organs, including spleen, lung, heart, kidney, liver, adrenal gland, brain, gastrointestinal system, pancreas, salivary gland, thymus and testis, from 8 week old ICE +/+, +/− and −/− animals showed no abnormalities. The ICE null mutation had no effect on the numbers of leukocytes, erythrocytes or platelets present in the peripheral blood. Additionally, there were no significant differences in various T cell subsets ($CD4^+CD8^+$, $CD4^+CD8^-$, $CD4^-CD8^+$, $CD4^-CD8^-$) and B cell subsets ($B220^+$) isolated from spleen, thymus and lymph nodes.

Figure 2:
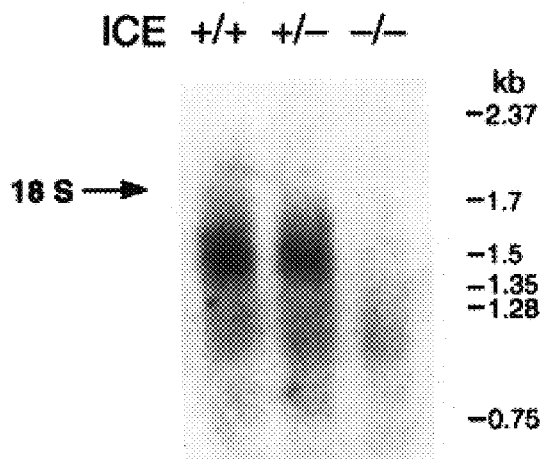
FIG. 2 is a photograph of a Northern blot depicting expression of ICE mRNA in spleen cells of wild type mice (+/+) or mice heterozygous (+/–) or homozygous (–/–) for the ICE gene disruption, demonstrating lack of expression of the full-length 1.6 kb ICE transcript in animals homozygous for the ICE mutation.

To confirm that the ICE −/− mice do not express full-length ICE mRNA transcripts, RNA was isolated from various tissues and analyzed by standard Northern hybridizations with an ICE cDNA probe or by reverse transcriptase-polymerase chain reaction (RT-PCR). RNA was extracted from various organs of the mice using 4M Guanidinium thiocyanate followed by centrifugation through 5.7 M CsCl as described in Sambrook et al. (*Molecular Cloning: A Laboratory Manual*, 2nd Edition, Cold Spring Harbor Laboratory press (1989)). The results of a Northern analysis of ICE mRNA expression in spleen is shown in FIG. 2, demonstrating that the full-length 1.6 kb ICE mRNA was not detectable in spleen from ICE −/− mice. A faint band in the 1–1.2 kb size range was seen consistently in ICE +/+, +/− and −/− animals, although the band appeared to be stronger in the heterozygous and homozygous lanes.

Figure 3:
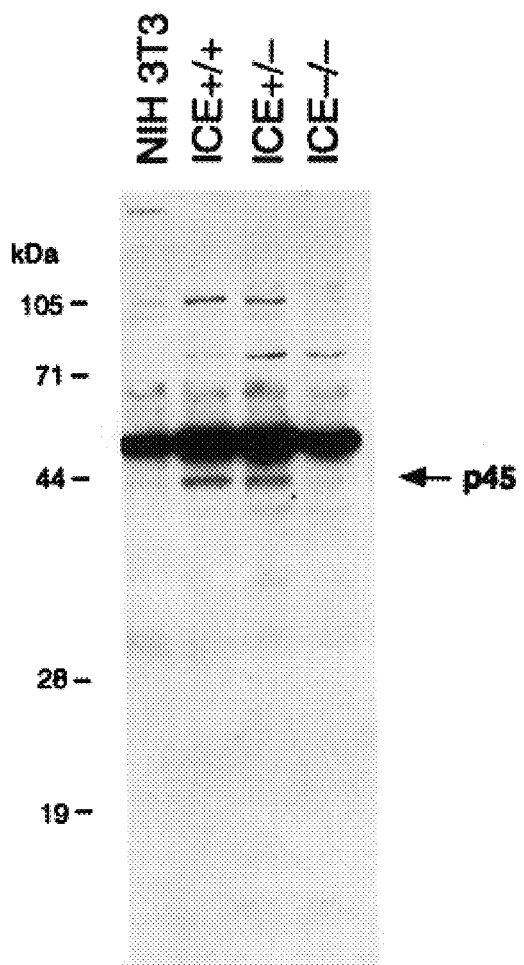
FIG. 3 is a photograph of a Western blot depicting expression of the ICE p45 protein in thioglycolate-elicited macrophages from wild type mice (+/+) or mice heterozygous (+/–) or homozygous (–/–) for the ICE gene disruption, demonstrating lack of expression of the ICE p45 protein in animals homozygous for the ICE mutation.

For RT-PCR analysis, first strand cDNA synthesis was made using the GIBCO BRL Superscript System according to the manufacturer's instructions. PCR was performed using a Perkin Elmer Thermal Cycler with oligonucleotide primers listed below in Table 1 and the following conditions: 95° 30 sec for 1 cycle; 94° 30 sec, 54° 30 sec, 72° 1 min for 30 cycles; and 72° 5 min for 1 cycle. PCR products were visualized by ethidium bromide on agarose gels. The results for a series of primer pairs that bind different regions of the ICE gene is shown below in Table 1:

cell lysates. 8 week old mice were injected i.p. with 1.5 ml of thioglycollate medium (commercially obtained from Sigma Chemical Co., St. Louis, Mo.). Peritoneal exudate cells (PECs) were harvested 4–5 days later. Macrophages were purified from the PECs by adherence to plastic in RPMI 1640 without serum for 2 hr at 37° C. Macrophage cell lysates were separated on 10% SDS-polyacrylamide gels, then transferred to nitrocellulose filters (commercially obtained from Amersham). Filters were probed with BBC2, a rabbit antibody to human ICE protein (amino acid residues 120–404), at 1 µg/ml in PBS with 5% dried milk and 0.2% Tween 20. Detection was carried out using a secondary, horse radish peroxidase-linked, anti-rabbit antibody (from Amersham) and the Amersham ECL system according to the manufacturer's instructions. The results are shown in FIG. 3. The 45 kDa ICE precursor protein was detectable in thioglycolate-elicited macrophage lysates from ICE +/+ and +/− mice, but not in lysates from negative control NIH 3T3

TABLE 1

RT-PCR Analysis of ICE +/+ (WT), ICE +/− (HET) and ICE −/− (HO) Mice

| 5' PRIMER | 3' PRIMER | WT | HET | HO |
|---|---|---|---|---|
| CCTGAGGGCAAAGAGGAAGC (ICE exon 2) (SEQ ID NO: 3) | TCTGAAGGATTTTCTTTCCA (ICE exon 4) (SEQ ID NO: 4) | + | + | + |
| CCTGAGGGCAAAGAGGAAGC (ICE exon 2) (SEQ ID NO: 3) | ATTTTCTTTCACTTTCACGG (ICE exon 5) (SEQ ID NO: 5) | + | + | + |
| CCTGAGGGCAAAGAGGAAGC (ICE exon 2) (SEQ ID NO: 3) | AAGGAAAGTACTGTAAGAAG (ICE exon 6; 5' of neo) (SEQ ID NO: 6) | + | + | + |
| CCTGAGGGCAAAGAGGAAGC (ICE exon 2) (SEQ ID NO: 3) | CATGCCTGAATAATGATCACC (ICE exon 6; 3' of neo) (SEQ ID NO: 7) | + | + | − |
| CCTGAGGGCAAAGAGGAAGC (ICE exon 2) (SEQ ID NO: 3) | GAGCAGAAAGCAATAAAATC (ICE exon 7) (SEQ ID NO: 8) | + | + | − |
| CCTGAGGGCAAAGAGGAAGC (ICE exon 2) (SEQ ID NO: 3) | AGCCTAAATTCTGGTTGTTC (ICE exon 9) (SEQ ID NO: 9) | + | + | − |
| CCTGAGGGCAAAGAGGAAGC (ICE exon 2) (SEQ ID NO: 3) | GGCACGATTCTCAGCATAGG (ICE exon 10) (SEQ ID NO: 10) | + | + | − |
| GGTGAAAGAGGTGAAAGAAT (ICE exon 6; 5' of neo) (SEQ ID NO: 11) | CATGCCTGAATAATGATCACC (ICE exon 6; 3' of neo) (SEQ ID NO: 7) | + | + | − |
| GCTATCGTGGCTGGCCACGA (Neomycin) (SEQ ID NO: 13) | CAACGCTATGTCCTGATAGC (Neomycin) (SEQ ID NO: 12) | − | + | + |
| TGCCTGCTTGCCGAATATCA (Neomycin) (SEQ ID NO: 14) | GAGCAGAAAGCAATAAAATC (ICE exon 7) (SEQ ID NO: 8) | − | + | + |
| TGCCTGCTTGCCGAATATCA (Neomycin) (SEQ ID NO: 14) | AGCCTAAATTCTGGTTGTTC (ICE exon 9) (SEQ ID NO: 9) | − | + | + |
| TGCCTGCTTGCCGAATATCA (Neomycin) (SEQ ID NO: 14) | AGCCTAAATTCTGGTTGTTC (ICE exon 9) (SEQ ID NO: 9) | − | + | + |

Primers specific for the neomycin gene detected a transcript in ICE +/− and −/− but not +/+ animals. Using a 5' primer specific for exon 2 and a series of 3' primers specific for each consecutive exon up to exon 10, only transcripts containing exons 2–5 were detected in ICE −/− animals. A 5' primer specific for the neo gene and a series of 3' primers specific for exons 7 to 9 also detected transcripts in ICE −/− and +/− animals. The results of the Northern and RT-PCT analyses confirm that homozygous disruption of the ICE gene results in an absence of detectable full-length ICE mRNA transcripts in the ICE −/− mice.

To examine ICE protein expression in the ICE deficient mice, Western blot analyses were performed on macrophage cells or in macrophage lysates from ICE −/− mice. These results confirm that homozygous disruption of the ICE gene results in an absence of detectable ICE protein in the −/− mice.

EXAMPLE 4

Disruption of the ICE Gene Affects IL-1β and IL-1α Secretion

To examine the effect of the ICE gene disruption on processing and release of IL-1β in vitro, thioglycolate-elicited macrophages were obtained from ICE +/+, +/− and −/− mice, stimulated in vitro with lipopolysaccharide (LPS)

to induce expression of preIL-1β and then treated with adenosine triphosphate (ATP), which has previously been shown to trigger efficient processing and release of matIL-1β from mouse macrophages (Hogquist, K. A. et al. (1991) *Proc. Natl. Acad. Sci. USA* 88:8485–8489; and Perregaux, D. and Gabel, C. A. (1994) *J. Biol. Chem.* 269:15195–15203). Peritoneal macrophages were stimulated with LPS (*Escherichia coli* strain 0111:B4, Calbiochem) at 1 µg/ml in RPMI 1640 with 10% fetal calf serum for 4 hr at 37° C., then treated with ATP (5 mM, Sigma) for 30 min, essentially as described by Hogquist et al. (cited supra). Fresh medium was added and the cells cultured for a further 3 hr. In some experiments, the tetrapeptide aldehyde Ac-YVAD-CHO (custom made by Bachem Bioscience), a specific inhibitor of ICE, or the tripeptide aldehyde leupeptin (Sigma), a control protease inhibitor that does not inhibit ICE, were present in the medium at 50 µM.

Following LPS and ATP stimulation of the macrophages, in the absence of presence of the peptide inhibitors, the levels of IL-1α and β in the medium were measured using commercially available ELISA assays (PerSeptive Diagnostics). The results are summarized below in Table 2:

To further examine the release of IL-1α and β in the ICE deficient mice, immunoprecipitations of the two cytokines were performed on cell lysates and media from pulse-chase, [$^{35}$S]methionine-labeled macrophages. Macrophages were treated with or without LPS (1 µg/ml) for 4 hr and pulse-labeled with [$^{35}$S]methionine (200 µCi/ml, Du Pont) during the fourth hour. Labeled cells were washed with PBS, treated with ATP (5 mM) for 30 min and the medium collected, fresh medium was added and then harvested after a further 3 hr chase. Cell lysates were prepared either before addition of ATP (time zero of chase) or at 3 hr post-ATP treatment (end of chase), by extraction with 1% Triton X-100, 50 mM Tris-HCl pH 8, 150 mM NaCl plus protease inhibitors [1 mM EGTA, 25 mM iodoacetamide, 100 µg/ml aprotinin, 100 µg/ml leupeptin, 10 µg/ml pepstatin and 1 mM phenylmethylsulfonyl fluoride (PMSF), (all from Sigma)]. Media samples were adjusted to 1% Triton X-100, 50 mM Tris-HCl pH 8, plus protease inhibitors. Cell lysates and media samples were precleared with normal goat immunoglobulin (Sigma) and protein G-sepharosc (Sigma). Immunoprecipitations were performed with goat antibodies specific for mouse IL-1α or IL-1β (R&D Systems). Immunoprecipitates bound on protein G-sepharose were washed five times with 1% Triton, 50 mM Tris-HCl pH 8, 150 mM

TABLE 2

IL-1α and β Release from ICE +/+, ICE +/- and ICE -/- Macrophages

| | IL-1α (pg/ml) | | | IL-1β (pg/ml) | | |
|---|---|---|---|---|---|---|
| Stimulation | ICE +/+ | ICE +/- | ICE -/- | ICE +/+ | ICE +/- | ICE -/- |
| LPS | 5845 ± 860 | 3511 ± 313 | 1199 ± 118 | 4428 ± 36 | 1879 ± 184 | <20 |
| LPS + YVAD | 4162 ± 399 | 3135 ± 243 | 941 ± 30 | 833 ± 40 | 332 ± 60 | <20 |
| LPS + Leupep. | 4241 ± 79 | 2971 ± 388 | 938 ± 12 | 4013 ± 262 | 2796 ± 123 | <20 |

While ICE +/+ and +/- mice efficiently released IL-1β upon stimulation with LPS and ATP, with levels of 2000 to 4000 pg/ml in the medium, the ICE -/- mice released essentially undetectable amounts of IL-1β (<20 pg/ml) into the medium. Unexpectedly, the release of IL-1α was also substantially reduced from ICE -/- macrophages, the level of IL-1α released by homozygous cells being only about 25% of that released from wild type and heterozygous cells.

The ICE inhibitor Ac-YVAD-CHO significantly inhibited the release of IL-1β, but not IL-1α, from +/+ and +/- macrophages, whereas the control inhibitor, leupeptin, did not significantly affect either IL-1β or α release. To quantitate the efficacy of Ac-YVAD-CHO in inhibiting ICE activity in LPS-treated ICE+/+ macrophages treated with the inhibitor, the amounts of matIL-1β released by the ICE +/+, +/- and -/- macrophages treated with LPS in the absence of the inhibitor can be used as standard controls. For example, the amount of matIL-1β released by LPS-treated +/+ macrophages (4428±36 pg/ml) is used as the 0% inhibition standard, the amount of matIL-1β released by LPS-treated+/- macrophages (1879±184 pg/ml) is used as the 50% inhibition standard and the amount of matIL-1β released by LPS-treated -/- macrophages (~20 pg/ml) is used as the 100% inhibition standard. These results are illustrated graphically in FIG. 5. The amount of matIL-1β released from LPS-treated ICE +/+ macrophages in the presence of Ac-YVAD-CHO (833±40 pg/ml) is then compared to these standards. When evaluated using the standard graph of FIG. 5, the percent inhibition of matIL-1β release from LPS-treated ICE +/+ macrophages by Ac-YVAD-CHO (50 µM) is 78%.

NaCl and 1 mM PMSF, then analyzed on 12% SDS polyacrylamide gels.

Figure 4A:
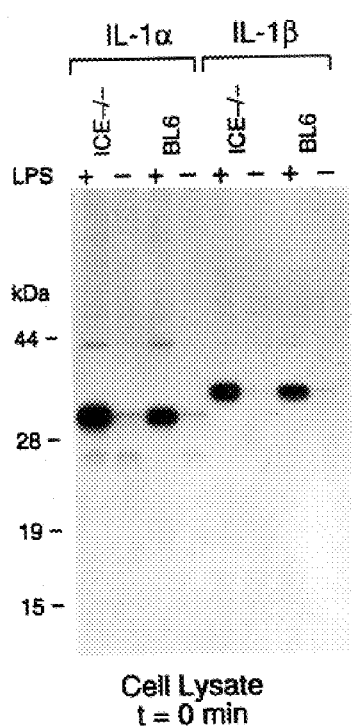
FIG. 4 is a photograph of immunoprecipitations of IL-1α and IL-1β from cell lysates and media of pulse-chase [$^{35}$S]methionine-labeled macrophages with and without LPS treatment, demonstrating lack of secretion of matIL-1β, and reduced secretion of matIL-1α, in animals homozygous for the ICE mutation.
Figure 4B:
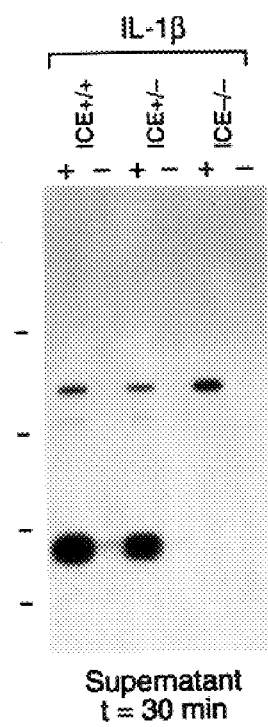
Figure 4C:
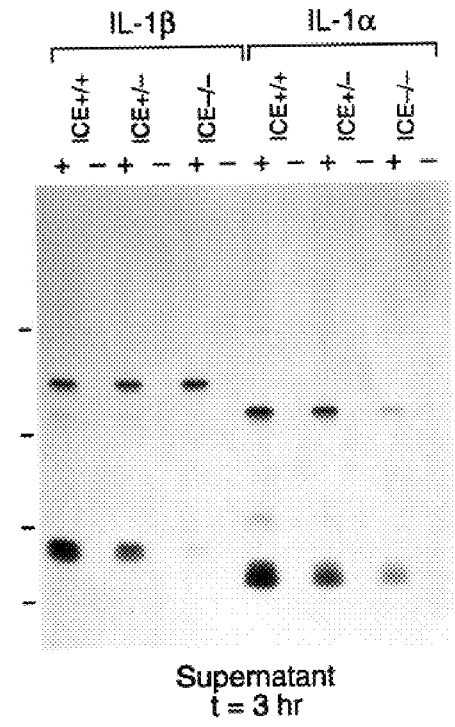

The results of the immunoprecipitation experiments are shown in FIG. 4. Analysis of the cell lysates demonstrated that induction by LPS of the 31 kDa IL-1α and 34 kDa IL-1β precursors intracellularly was similar in C57BL/6 and ICE -/- macrophages, indicating that the ICE gene disruption did not affect the expression of the precursor forms of the cytokines. (Similar results were observed for ICE +/+ and +/- macrophages). In contrast, analysis of the medium demonstrated that no secreted 17 kDa mature IL-1β was detectable from LPS-stimulated macrophages from ICE -/- mice after 30 minutes of ATP treatment. Upon a further 3 hour culture, after removal of ATP, a trace level of 17 kDa IL-1β was found in the medium of ICE -/- macrophages. Immunoprecipitations of IL-1α at the 3 hour time point showed that levels of both the 31 kDa precursor and the 15 kDa processed form of IL-1α were significantly reduced in the medium of ICE -/- macrophages compared to the levels observed in media of ICE +/+ or +/- macrophages.

In summary, the above-described experiments demonstrate that homozygous disruption of the ICE gene in macrophages from the ICE -/- mice reduces the amount of secreted matIL-1β following stimulation to essentially undetectable levels, whereas heterozygous disruption of the ICE gene in macrophages from the ICE +/- mice reduces the amount of secreted matIL-1β following stimulation to approximately 50% of the wild type level. Moreover, the ICE deficient animals exhibited an unexpected and marked reduction in the levels of secreted preIL-1α and matIL-1α, suggesting a role for ICE and/or IL-1β in the processing and/or release of IL-1α.

EXAMPLE 5

Disruption of the ICE Gene Does Not Affect Apoptosis

To examine whether disruption of the ICE gene had an affect on apoptosis in ICE –/– mice, two cell types from the mice, macrophages and thymocytes, were examined for susceptibility to apoptosis in vitro. Since ATP treatment of macrophages had been reported to induce apoptosis in addition to IL-1 release (Hogquist, K. A. et al. (1991) *Proc. Natl. Acad. Sci. USA* 88:8485–8489), macrophages treated with ATP as described in Example 4 were analyzed for DNA fragmentation as an indicator of apoptosis. ATP treatment induced DNA fragmentation equally efficiently in C57BL/6 and ICE –/– macrophages. Thus, the ICE deficient macrophages did not appear to be impaired for ATP-induced apoptosis.

Figure 6:
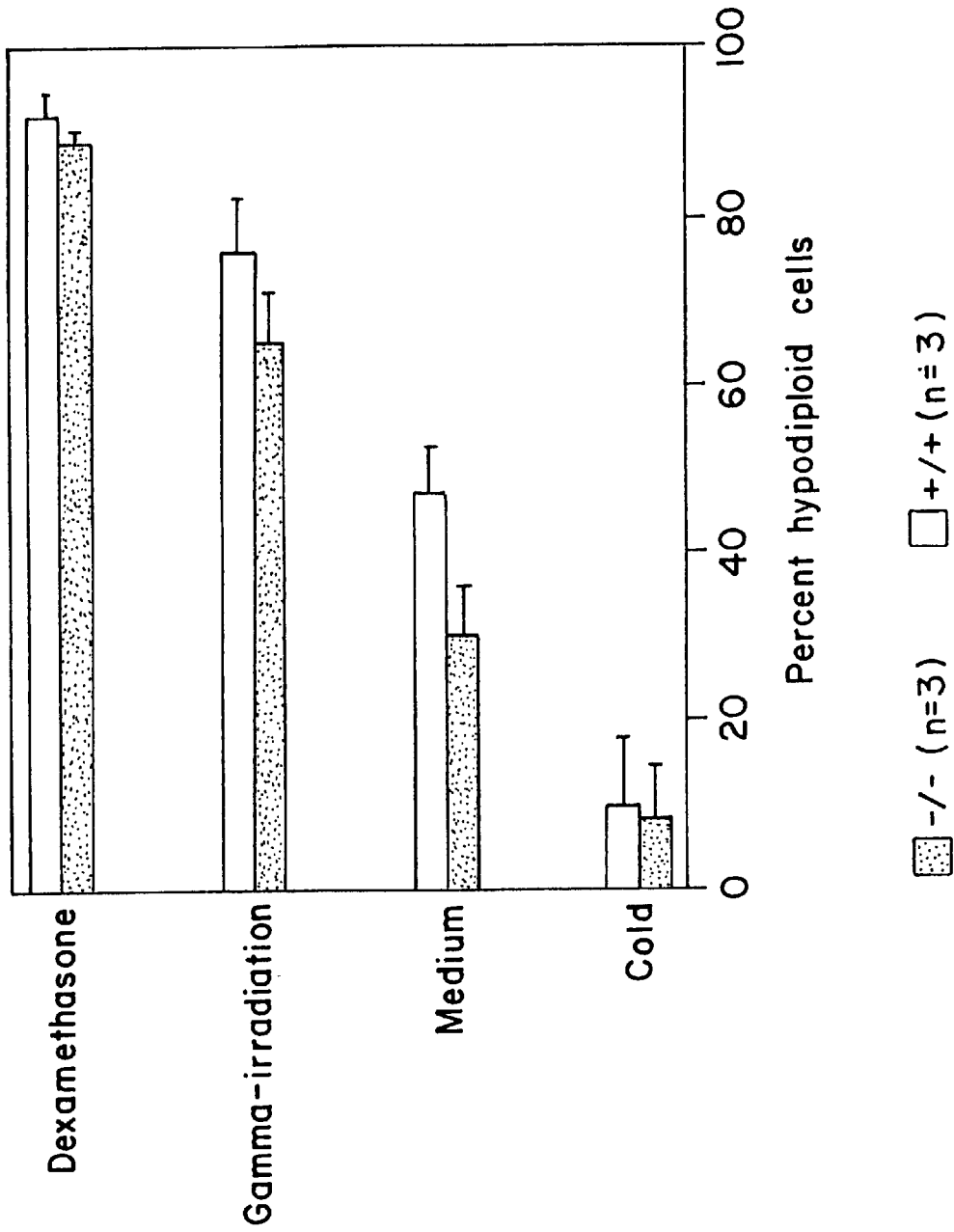
FIG. 6 is a graphic representation of the percent apoptosis, as measured by percent hypodiploid cells, in thymocytes from ICE +/+ and –/– mice, demonstrating that the ICE mutation does not prevent apoptosis. The thymocytes were either untreated (medium), incubated at 4° C. (cold), treated with dexamethasone, or gamma irradiated.

Apoptosis was also examined in thymocytes from ICE –/– mice that had been exposed to either dexamethasone or gamma-irradiation. Thymocytes were isolated and incubated in RPMI with 10% fetal calf serum and supplements at a concentration of $2 \times 10^6$ cells/ml in vitro in 48-well tissue culture plates (Costar), at 37° C. in a 5% $CO_2$ incubator. They were incubated with or without dexamethasone at $10^{-6}$ M, or were gamma-irradiated with 5 Gy prior to culture. Some cells were kept at 4° C. to prevent apoptosis. The cells were collected after 18 h culture in vitro, and apoptosis was analyzed by determining the percent of hypodiploid cells using propidium iodide staining as follows. The cells were fixed with 70% ethanol for 1 h at 4° C., washed, and then treated with RNAse (0.5 mg/ml) and propidium iodide (PI) (50 μg/ml) as described in Nicoletti, I. et al. (1991) *J. Immunol. Methods* 139:271–279. The cells were stored in the dark at 4° C. until they were analyzed on a FACScan flow cytometer for PI fluorescence using CellFit software. The percent of cells with hypodiploid staining of the nuclei was taken as a measure of apoptosis (Nicoletti, I. et al. (1991), cited supra). As shown in FIG. 6, apoptosis was observed in ICE –/– thymocytes after treatment in vitro with either dexamethasone or gamma-irradiation. The percent apoptotic cells were similar in the ICE –/– and +/+ mice.

Thus, in summary, apoptosis in two cell types examined was not affected by disruption of the ICE gene. While ICE has previously been implicated in the induction of apoptosis (see e.g., Gagliardini, V. et al. (1994) *Science* 263:826), the results described herein suggest that either ICE is not involved in apoptosis or that other proteins still present in the ICE deficient mice can compensate for the ICE defect with regard to apoptosis.

EXAMPLE 6

Disruption of the ICE Gene Provides Resistance to LPS-Induced Septic Shock

Injection of high dose LPS intraperitoneally is known to induce a massive systemic release of proinflammatory cytokines such as IL-1 and TNF-α. These cytokines are considered to be crucial in the pathogenesis of septic shock or systemic inflammatory response syndrome (SIRS) leading to death in mice. To investigate whether the ICE deficient mice have a defect in in vivo IL-1 production, and if this defect leads to decreased systemic inflammatory responses, the lethality of ICE –/– mice in this model of SIRS induced by high dose LPS was examined. 8–10 weeks old mice were injected with 800 μg of LPS (from *Escherichia coli* serotype 0111:B4, obtained from Calbiochem Corporation, La Jolla, Calif.) intraperitoneally to induce high-dose LPS-induced septic shock. This dose of LPS (800 μg) was previously found to cause 100% lethality in C57BL/6 mice. The mice were monitored at least twice daily for 4 days and periodically thereafter.

Figure 7:
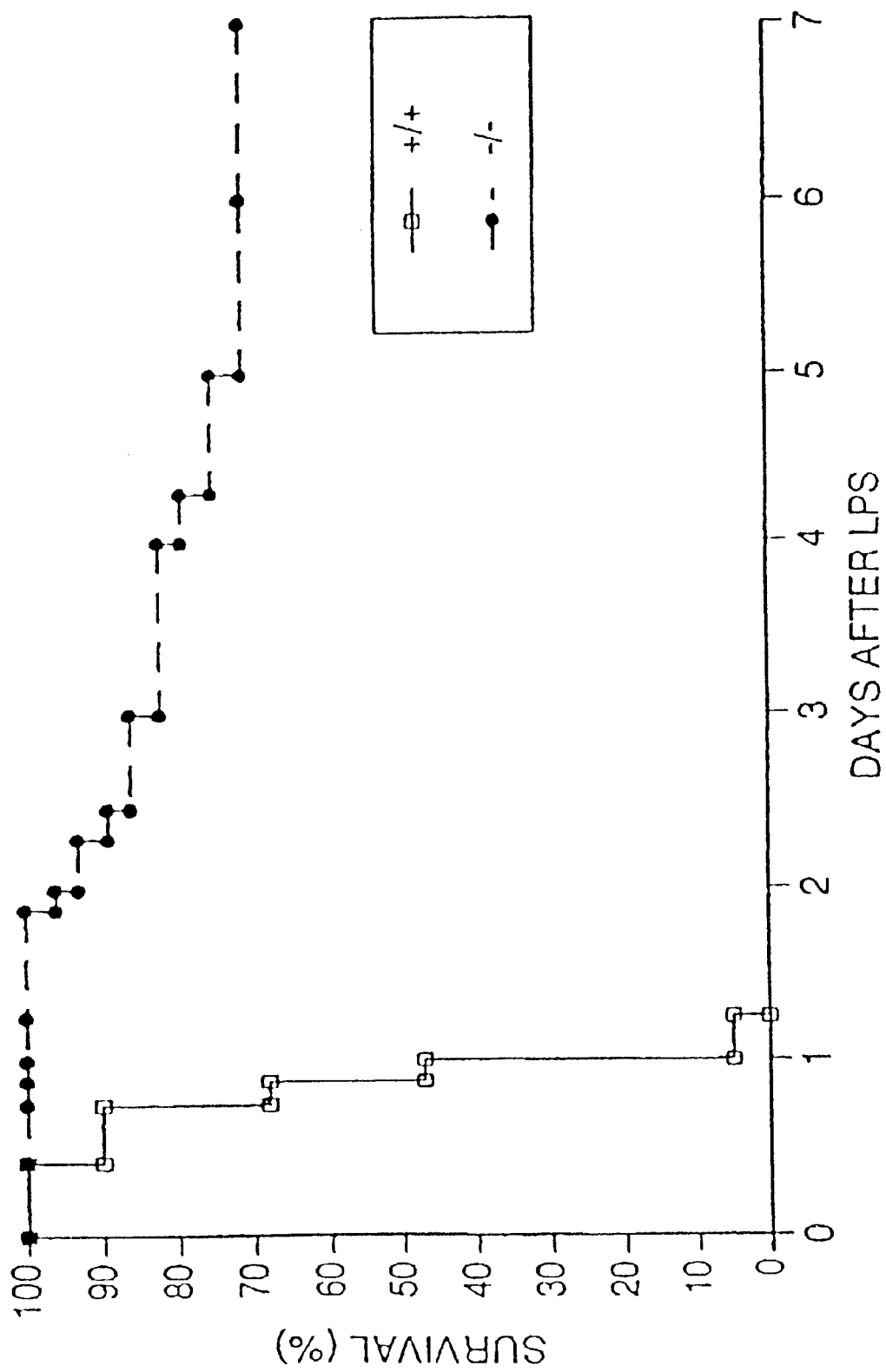
FIG. 7 is a graphic representation of the survival of ICE +/+ and –/– mice after high dose LPS-induced septic shock, demonstrating that animals homozygous for the ICE gene mutation exhibit resistance to septic shock.

All ICE +/+ mice succumbed to the high dose LPS within 30 hours. In contrast, the ICE –/– mice were highly resistant to the lethal effects of LPS, with 70% of the mice surviving after 7 days. The survival results are illustrated graphically in FIG. 7. The data in FIG. 7 are combined from three independent experiments, with a total of 28 –/– and 19 +/+ mice. The results show that the survival of –/– mice was significantly enhanced (p<0.001 by the chi-squared test) as compared to the +/+ mice. The minority of ICE –/– mice that died had a delayed mortality compared to the ICE +/+ mice, with the first death in the former group occurring at around 45 hours in each experiment. The ICE –/– mice did demonstrate signs of endotoxemia, such as lethargy, piloerection and mild febrile shaking for the first few days after LPS injection. These signs, however, were milder compared to those in ICE +/+ mice at similar time points.

The release of inflammatory cytokines into the circulation of mice undergoing LPS-induced SIRS was also examined. 4h after LPS injection, the animals were bled (=100 μl) and plasma was pooled from animals of the same sex and genotype in order to obtain sufficient sample volume and analyzed for cytokines. Estimations of cytokine concentrations in the plasma of untreated and LPS treated ICE +/+ and –/– mice were obtained using commercially available EL,ISA kits. The ELISA kits for estimation of murine IL-1α, IL-1β, and TNF-α were purchased from Genzyme Corporation, Cambridge, Mass. The ELISA kit for estimation of murine IL-6 was purchased from Biosource International, Camarillo, Calif. Using the methods described in the kits according to the manufacturer's instructions and with the dilutions used for the assays, the detection limits for IL-1β and IL-1α were 20 pg/ml and 30 pg/ml, respectively. Representative cytokine data from one of three experiments is shown below in Table 3:

TABLE 3

Cytokine Concentrations in Plasma of LPS-Stimulated ICE +/+ and ICE –/– Mice

| Cytokines | Females | | Males | |
| --- | --- | --- | --- | --- |
| | ICE +/+ | ICE –/– | ICE +/+ | ICE –/– |
| IL-1β (pg/ml) | 493 ± 34 | <20 | 126 ± 2 | <20 |
| IL-1α (pg/ml) | 253 ± 18 | <30 | 62 ± 8 | <30 |
| TNFα (pg/ml) | 884 ± 56 | 627 ± 150 | 821 ± 12 | 562 ± 78 |
| IL-6 (ng/ml) | 520 ± 71 | 296 ± 16 | 209 ± 49 | 179 ± 12 |

IL-1β was undetectable in the plasma of ICE –/– mice injected with LPS in three separate experiments, whereas this cytokine was detectable at high levels in the ICE +/+ mice in each experiment. Consistent with the results observed with macrophages stimulated with LPS and ATP in vitro, described in Example 4, the levels of IL-1α in the plasma of LPS-treated ICE –/– mice were unexpectedly very low or undetectable compared to the ICE +/+ mice. TNFα and IL-6 were readily detectable in the ICE –/– mice and the concentration levels were only somewhat lower than in the ICE +/+ mice. Although the female ICE +/+ mice had higher IL-1β and IL-1α levels compared to male ICE +/+ mice, the time of death or susceptibility to death due to SIRS did not correlate with sex in either genotype.

The above-described results demonstrate that ICE −/− mice are highly resistant to the lethal effects of septic shock induced by high dose LPS injection. The results of these experiments, together with those described for matIL-1β production by macrophages in Example 4, definitively demonstrate that ICE is the primary protease responsible for generation of matIL-1β in vivo

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A transgenic knockout mouse whose genome comprises a homozygous disruption in its endogenous Interleukin-1β converting enzyme (ICE) gene, wherein said homozygous disruption prevents the expression of a functional ICE protein, and wherein said homozygous disruption results in said transgenic knockout mouse exhibiting decreased levels of mature IL-1α and IL-1β as compared to a wild-type mouse.

2. The transgenic knockout mouse of claim 1, wherein the homozygous disruption results from insertion of a positive selection expression cassette into the endogenous ICE gene.

3. The transgenic knockout mouse of claim 2, wherein the positive selection expression cassette comprises a neomycin phosphotransferase gene operatively linked to at least one regulatory element.

4. The transgenic knockout mouse of claim 2, wherein the positive selection expression cassette is inserted into exon 6 of the endogenous ICE gene.

5. A method for producing a transgenic knockout mouse exhibiting decreased levels of mature IL-1α and IL-1β relative to a wild-type mouse, said method comprising:

(a) introducing an ICE targeting vector into a mouse embryonic stem cell;

(b) introducing said mouse embryonic stem cell into a mouse blastocyst;

(c) transplanting said mouse blastocyst into a pseudopregnant mouse;

(d) allowing said transplanted mouse blastocyst to develop to term;

(e) identifying a transgenic mouse whose genome comprises a disruption of the endogenous ICE gene in at least one allele;

(f) breeding the transgenic mouse of step (e) to obtain a transgenic mouse whose genome comprises a homozygous disruption of the endogenous ICE gene, wherein said disruption results in said transgenic mouse exhibiting decreased levels of mature IL-1α and IL-1β relative to a wild-type mouse.

6. The method of claim 5, wherein said ICE targeting vector comprises a positive selection expression cassette.

7. The method claim 6, wherein the positive selection expression cassette comprises a neomycin phosphotransferase gene operatively linked to at least one regulatory element.

8. The method claim 6, wherein the positive selection expression cassette is inserted into exon 6 of the endogenous ICE gene.

9. A transgenic knockout mouse produced by the method of claim 5, wherein the genome of said transgenic knockout mouse comprises a homozygous disruption of the endogenous ICE gene, and wherein said disruption results in said transgenic knockout mouse exhibiting decreased levels of mature IL-1α and IL-1β relative to a wild-type mouse.

* * * * *

```
                        SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO:1:

GATCCGAACC CCTTCGCATG                                                   20

(2) INFORMATION FOR SEQ ID NO:2:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO:2:

CGAAGGGGTT CG                                                           12

(2) INFORMATION FOR SEQ ID NO:3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO:3:

CCTGAGGGCA AAGAGGAAGC                                                   20

(2) INFORMATION FOR SEQ ID NO:4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: oligonucleotide (xi) SEQUENCE DESCRIPTION: SEQ ID NO:4:

TCTGAAGGAT TTTCTTTCCA                                                   20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ATTTTCTTTC ACTTTCACGG                                        20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

AAGGAAAGTA CTGTAAGAAG                                        20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

CATGCCTGAA TAATGATCAC C                                       21

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

GAGCAGAAAG CAATAAAATC                                        20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

AGCCTAAATT CTGGTTGTTC                                        20

(2) INFORMATION FOR SEQ ID NO:10:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:10:

GGCACGATTC TCAGCATAGG                                                    20

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:11:

GGTGAAAGAG GTGAAAGAAT                                                    20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:12:

CAACGCTATG TCCTGATAGC                                                    20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:13:

GCTATCGTGG CTGGCCACGA                                                    20

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:14:

TGCCTGCTTG CCGAATATCA                                                    20

(2) INFORMATION FOR SEQ ID NO:15:

(i) SEQUENCE CHARACTERISTICS:
            (A) LENGTH: 1335 base pairs
            (B) TYPE: nucleic acid
            (C) STRANDEDNESS: single
            (D) TOPOLOGY: linear (ii) MOLECULE TYPE: cDNA (ix) FEATURE:
   (A) NAME/KEY: CDS
   (B) LOCATION: 1..1209

(xi) SEQUENCE DESCRIPTION: SEQ ID NO:15:

| | | | | | | | | | | | | | | | | |
|---|---|---|---|---|---|---|---|---|---|---|---|---|---|---|---|---|
| ATG | GCT | GAC | AAG | ATC | CTG | AGG | GCA | AAG | AGG | AAG | CAA | TTT | ATC | AAC | TCA | 48 |
| Met | Ala | Asp | Lys | Ile | Leu | Arg | Ala | Lys | Arg | Lys | Gln | Phe | Ile | Asn | Ser | |
| 1 | | | | 5 | | | | | 10 | | | | | 15 | | |
| GTG | AGT | ATA | GGG | ACA | ATA | AAT | GGA | TTG | TTG | GAT | GAA | CTT | TTA | GAG | AAG | 96 |
| Val | Ser | Ile | Gly | Thr | Ile | Asn | Gly | Leu | Leu | Asp | Glu | Leu | Leu | Glu | Lys | |
| | | | 20 | | | | | 25 | | | | | 30 | | | |
| AGA | GTG | CTG | AAT | CAG | GAA | GAA | ATG | GAT | AAA | ATA | AAA | CTT | GCA | AAC | ATT | 144 |
| Arg | Val | Leu | Asn | Gln | Glu | Glu | Met | Asp | Lys | Ile | Lys | Leu | Ala | Asn | Ile | |
| | | 35 | | | | | 40 | | | | | 45 | | | | |
| ACT | GCT | ATG | GAC | AAG | GCA | CGG | GAC | CTA | TGT | GAT | CAT | GTC | TCT | AAA | AAA | 192 |
| Thr | Ala | Met | Asp | Lys | Ala | Arg | Asp | Leu | Cys | Asp | His | Val | Ser | Lys | Lys | |
| | 50 | | | | | 55 | | | | | 60 | | | | | |
| GGG | CCC | CAG | GCA | AGC | CAA | ATC | TTT | ATC | ACT | TAC | ATT | TGT | AAT | GAA | GAC | 240 |
| Gly | Pro | Gln | Ala | Ser | Gln | Ile | Phe | Ile | Thr | Tyr | Ile | Cys | Asn | Glu | Asp | |
| 65 | | | | | 70 | | | | | 75 | | | | | 80 | |
| TGC | TAC | CTG | GCA | GGA | ATT | CTG | GAG | CTT | CAA | TCA | GCT | CCA | TCA | GCT | GAA | 288 |
| Cys | Tyr | Leu | Ala | Gly | Ile | Leu | Glu | Leu | Gln | Ser | Ala | Pro | Ser | Ala | Glu | |
| | | | | 85 | | | | | 90 | | | | | 95 | | |
| ACA | TTT | GTT | GCT | ACA | GAA | GAT | TCT | AAA | GGA | GGA | CAT | CCT | TCA | TCC | TCA | 336 |
| Thr | Phe | Val | Ala | Thr | Glu | Asp | Ser | Lys | Gly | Gly | His | Pro | Ser | Ser | Ser | |
| | | | 100 | | | | | 105 | | | | | 110 | | | |
| GAA | ACA | AAG | GAA | GAA | CAG | AAC | AAA | GAA | GAT | GGC | ACA | TTT | CCA | GGA | CTG | 384 |
| Glu | Thr | Lys | Glu | Glu | Gln | Asn | Lys | Glu | Asp | Gly | Thr | Phe | Pro | Gly | Leu | |
| | | 115 | | | | | 120 | | | | | 125 | | | | |
| ACT | GGG | ACC | CTC | AAG | TTT | TGC | CCT | TTA | GAA | AAA | GCC | CAG | AAG | TTA | TGG | 432 |
| Thr | Gly | Thr | Leu | Lys | Phe | Cys | Pro | Leu | Glu | Lys | Ala | Gln | Lys | Leu | Trp | |
| | 130 | | | | | 135 | | | | | 140 | | | | | |
| AAA | GAA | AAT | CCT | TCA | GAG | ATT | TAT | CCA | ATA | ATG | AAT | ACA | ACC | ACT | CGT | 480 |
| Lys | Glu | Asn | Pro | Ser | Glu | Ile | Tyr | Pro | Ile | Met | Asn | Thr | Thr | Thr | Arg | |
| 145 | | | | | 150 | | | | | 155 | | | | | 160 | |
| ACA | CGT | CTT | GCC | CTC | ATT | ATC | TGC | AAC | ACA | GAG | TTT | CAA | CAT | CTT | TCT | 528 |
| Thr | Arg | Leu | Ala | Leu | Ile | Ile | Cys | Asn | Thr | Glu | Phe | Gln | His | Leu | Ser | |
| | | | | 165 | | | | | 170 | | | | | 175 | | |
| CCG | AGG | GTT | GGA | GCT | CAA | GTT | GAC | CTC | AGA | GAA | ATG | AAG | TTG | CTG | CTG | 576 |
| Pro | Arg | Val | Gly | Ala | Gln | Val | Asp | Leu | Arg | Glu | Met | Lys | Leu | Leu | Leu | |
| | | | 180 | | | | | 185 | | | | | 190 | | | |
| GAG | GAT | CTG | GGG | TAT | ACC | GTG | AAA | GTG | AAA | GAA | AAT | CTC | ACA | GCT | CTG | 624 |
| Glu | Asp | Leu | Gly | Tyr | Thr | Val | Lys | Val | Lys | Glu | Asn | Leu | Thr | Ala | Leu | |
| | | 195 | | | | | 200 | | | | | 205 | | | | |
| GAG | ATG | GTG | AAA | GAG | GTG | AAA | GAA | TTT | GCT | GCC | TGC | CCA | GAG | CAC | AAG | 672 |
| Glu | Met | Val | Lys | Glu | Val | Lys | Glu | Phe | Ala | Ala | Cys | Pro | Glu | His | Lys | |
| | 210 | | | | | 215 | | | | | 220 | | | | | |
| ACT | TCT | GAC | AGT | ACT | TTC | CTT | GTA | TTC | ATG | TCT | CAT | GGT | ATC | CAG | GAG | 720 |
| Thr | Ser | Asp | Ser | Thr | Phe | Leu | Val | Phe | Met | Ser | His | Gly | Ile | Gln | Glu | |
| 225 | | | | | 230 | | | | | 235 | | | | | 240 | |
| GGA | ATA | TGT | GGG | ACC | ACA | TAC | TCT | AAT | GAA | GTT | TCA | GAT | ATT | TTA | AAG | 768 |
| Gly | Ile | Cys | Gly | Thr | Thr | Tyr | Ser | Asn | Glu | Val | Ser | Asp | Ile | Leu | Lys | |
| | | | | 245 | | | | | 250 | | | | | 255 | | |
| GTT | GAC | ACA | ATC | TTT | CAG | ATG | ATG | AAC | ACT | TTG | AAG | TGC | CCA | AGC | TTG | 816 |
| Val | Asp | Thr | Ile | Phe | Gln | Met | Met | Asn | Thr | Leu | Lys | Cys | Pro | Ser | Leu | |
| | | | 260 | | | | | 265 | | | | | 270 | | | |
| AAA | GAC | AAG | CCC | AAG | GTG | ATC | ATT | ATT | CAG | GCA | TGC | CGT | GGA | GAG | AAA | 864 |
| Lys | Asp | Lys | Pro | Lys | Val | Ile | Ile | Ile | Gln | Ala | Cys | Arg | Gly | Glu | Lys | |

```
            275                 280                 285
CAA GGA GTG GTG TTG TTA AAA GAT TCA GTA AGA GAC TCT GAA GAG GAT      912
Gln Gly Val Val Leu Leu Lys Asp Ser Val Arg Asp Ser Glu Glu Asp
        290                 295                 300

TTC TTA ACG GAT GCA ATT TTT GAA GAT GAT GGC ATT AAG AAG GCC CAT      960
Phe Leu Thr Asp Ala Ile Phe Glu Asp Asp Gly Ile Lys Lys Ala His
305                 310                 315                 320

ATA GAG AAA GAT TTT ATT GCT TTC TGC TCT TCA ACA CCA GAT AAT GTG     1008
Ile Glu Lys Asp Phe Ile Ala Phe Cys Ser Ser Thr Pro Asp Asn Val
                325                 330                 335

TCT TGG AGA CAT CCT GTC AGG GGC TCA CTT TTC ATT GAG TCA CTC ATC     1056
Ser Trp Arg His Pro Val Arg Gly Ser Leu Phe Ile Glu Ser Leu Ile
            340                 345                 350

AAA CAC ATG AAA GAA TAT GCC TGG TCT TGT GAC TTG GAG GAC ATT TTC     1104
Lys His Met Lys Glu Tyr Ala Trp Ser Cys Asp Leu Glu Asp Ile Phe
        355                 360                 365

AGA AAG GTT CGA TTT TCA TTT GAA CAA CCA GAA TTT AGG CTA CAG ATG     1152
Arg Lys Val Arg Phe Ser Phe Glu Gln Pro Glu Phe Arg Leu Gln Met
370                 375                 380

CCC ACT GCT GAT AGG GTG ACC CTG ACA AAA CGT TTC TAC CTC TTC CCG     1200
Pro Thr Ala Asp Arg Val Thr Leu Thr Lys Arg Phe Tyr Leu Phe Pro
385                 390                 395                 400

GGA CAT TAAACGAAGA ATCCAGTTCA TTCTTATGTA CCTATGCTGA GAATCGTGCC     1256
Gly His

AATAAGAAGC CAATACTTCC TTAGATGATG CAATAAATAT TAAAATAAAA CAAAACAGAA   1316

AGGCTAAAAA AAAAAAAAA                                                1335

(2) INFORMATION FOR SEQ ID NO:16:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:16:

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
    50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
    130                 135                 140

Lys Glu Asn Pro Ser Glu Ile Tyr Pro Ile Met Asn Thr Thr Thr Arg
145                 150                 155                 160
```

```
Thr Arg Leu Ala Leu Ile Ile Cys Asn Thr Glu Phe Gln His Leu Ser
            165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
            195                 200                 205

Glu Met Val Lys Glu Val Lys Glu Phe Ala Ala Cys Pro Glu His Lys
            210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
            245                 250                 255

Val Asp Thr Ile Phe Gln Met Met Asn Thr Leu Lys Cys Pro Ser Leu
            260                 265                 270

Lys Asp Lys Pro Lys Val Ile Ile Gln Ala Cys Arg Gly Glu Lys
            275                 280                 285

Gln Gly Val Val Leu Leu Lys Asp Ser Val Arg Asp Ser Glu Glu Asp
            290                 295                 300

Phe Leu Thr Asp Ala Ile Phe Glu Asp Asp Gly Ile Lys Lys Ala His
305                 310                 315                 320

Ile Glu Lys Asp Phe Ile Ala Phe Cys Ser Ser Thr Pro Asp Asn Val
            325                 330                 335

Ser Trp Arg His Pro Val Arg Gly Ser Leu Phe Ile Glu Ser Leu Ile
            340                 345                 350

Lys His Met Lys Glu Tyr Ala Trp Ser Cys Asp Leu Glu Asp Ile Phe
            355                 360                 365

Arg Lys Val Arg Phe Ser Phe Glu Gln Pro Glu Phe Arg Leu Gln Met
            370                 375                 380

Pro Thr Ala Asp Arg Val Thr Leu Thr Lys Arg Phe Tyr Leu Phe Pro
385                 390                 395                 400

Gly His (2) INFORMATION FOR SEQ ID NO:17:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1212

(xi) SEQUENCE DESCRIPTION: SEQ ID NO:17:

ATG GCC GAC AAG GTC CTG AAG GAG AAG AGA AAG CTG TTT ATC CGT TCC        48
Met Ala Asp Lys Val Leu Lys Glu Lys Arg Lys Leu Phe Ile Arg Ser
  1               5                  10                  15

ATG GGT GAA GGT ACA ATA AAT GGC TTA CTG GAT GAA TTA TTA CAG ACA        96
Met Gly Glu Gly Thr Ile Asn Gly Leu Leu Asp Glu Leu Leu Gln Thr
             20                  25                  30

AGG GTG CTG AAC AAG GAA GAG ATG GAG AAA GTA AAA CGT GAA AAT GCT       144
Arg Val Leu Asn Lys Glu Glu Met Glu Lys Val Lys Arg Glu Asn Ala
         35                  40                  45

ACA GTT ATG GAT AAG ACC CGA GCT TTG ATT GAC TCC GTT ATT CCG AAA       192
Thr Val Met Asp Lys Thr Arg Ala Leu Ile Asp Ser Val Ile Pro Lys
     50                  55                  60
```

```
GGG GCA CAG GCA TGC CAA ATT TGC ATC ACA TAC ATT TGT GAA GAA GAC          240
Gly Ala Gln Ala Cys Gln Ile Cys Ile Thr Tyr Ile Cys Glu Glu Asp
 65              70                  75                  80

AGT TAC CTG GCA GGG ACG CTG GGA CTC TCA GCA GAT CAA ACA TCT GGA          288
Ser Tyr Leu Ala Gly Thr Leu Gly Leu Ser Ala Asp Gln Thr Ser Gly
                     85                  90                  95

AAT TAC CTT AAT ATG CAA GAC TCT CAA GGA GTA CTT TCT TCC TTT CCA          336
Asn Tyr Leu Asn Met Gln Asp Ser Gln Gly Val Leu Ser Ser Phe Pro
                100                 105                 110

GCT CCA CAG GCA GTG CAG GAC AAC CCG GCT ATG CCG ACC TCT TCT GGT          384
Ala Pro Gln Ala Val Gln Asp Asn Pro Ala Met Pro Thr Ser Ser Gly
            115                 120                 125

TCT GAA GGT AAC GTT AAA CTG TGC TCT CTG GAA GAA GCT CAA AGG ATA          432
Ser Glu Gly Asn Val Lys Leu Cys Ser Leu Glu Glu Ala Gln Arg Ile
        130                 135                 140

TGG AAA CAA AAG TCG GCA GAG ATT TAT CCA ATA ATG GAC AAG TCA AGC          480
Trp Lys Gln Lys Ser Ala Glu Ile Tyr Pro Ile Met Asp Lys Ser Ser
145                 150                 155                 160

CGC ACA CGT CTT GCT CTC ATT ATC TGC AAT GAA GAA TTT GAC AGT ATT          528
Arg Thr Arg Leu Ala Leu Ile Ile Cys Asn Glu Glu Phe Asp Ser Ile
                165                 170                 175

CCT AGA AGA ACT GGA GCT GAG GTT GAC ATC ACA GGC ATG ACA ATG CTG          576
Pro Arg Arg Thr Gly Ala Glu Val Asp Ile Thr Gly Met Thr Met Leu
            180                 185                 190

CTA CAA AAT CTG GGG TAC AGC GTA GAT GTG AAA AAA AAT CTC ACT GCT          624
Leu Gln Asn Leu Gly Tyr Ser Val Asp Val Lys Lys Asn Leu Thr Ala
        195                 200                 205

TCG GAC ATG ACT ACA GAG CTG GAG GCA TTT GCA CAC CGC CCA GAG CAC          672
Ser Asp Met Thr Thr Glu Leu Glu Ala Phe Ala His Arg Pro Glu His
210                 215                 220

AAG ACC TCT GAC AGC ACG TTC CTG GTG TTC ATG TCT CAT GGT ATT CGG          720
Lys Thr Ser Asp Ser Thr Phe Leu Val Phe Met Ser His Gly Ile Arg
225                 230                 235                 240

GAA GGC ATT TGT GGG AAG AAA CAC TCT GAG CAA GTC CCA GAT ATA CTA          768
Glu Gly Ile Cys Gly Lys Lys His Ser Glu Gln Val Pro Asp Ile Leu
                245                 250                 255

CAA CTC AAT GCA ATC TTT AAC ATG TTG AAT ACC AAG AAC TGC CCA AGT          816
Gln Leu Asn Ala Ile Phe Asn Met Leu Asn Thr Lys Asn Cys Pro Ser
            260                 265                 270

TTG AAG GAC AAA CCG AAG GTG ATC ATC ATC CAG GCC TGC CGT GGT GAC          864
Leu Lys Asp Lys Pro Lys Val Ile Ile Ile Gln Ala Cys Arg Gly Asp
        275                 280                 285

AGC CCT GGT GTG GTG TGG TTT AAA GAT TCA GTA GGA GTT TCT GGA AAC          912
Ser Pro Gly Val Val Trp Phe Lys Asp Ser Val Gly Val Ser Gly Asn
290                 295                 300

CTA TCT TTA CCA ACT ACA GAA GAG TTT GAG GAT GAT GCT ATC AAA AAA          960
Leu Ser Leu Pro Thr Thr Glu Glu Phe Glu Asp Asp Ala Ile Lys Lys
305                 310                 315                 320

GCT CAC ATC GAA AAA GAC TTC ATC GCT TTC TGC TCT TCC ACA CCA GAT         1008
Ala His Ile Glu Lys Asp Phe Ile Ala Phe Cys Ser Ser Thr Pro Asp
                325                 330                 335

AAT GTT TCT TGG AGA CAT CCC ACA ATG GGC TCT GTT TTT ATT GGA AGA         1056
Asn Val Ser Trp Arg His Pro Thr Met Gly Ser Val Phe Ile Gly Arg
            340                 345                 350

CTC ATT GAA CAT ATG CAA GAA TAT GCC TGT TCC TGT GAT GTG GAG GAA         1104
Leu Ile Glu His Met Gln Glu Tyr Ala Cys Ser Cys Asp Val Glu Glu
        355                 360                 365

ATT TTC CGC AAG GTT CGA TTT TCA TTT GAG CAG CCA GAT GGT AGA GCG         1152
Ile Phe Arg Lys Val Arg Phe Ser Phe Glu Gln Pro Asp Gly Arg Ala
```

```
                    370                 375                 380
CAG ATG CCC ACC ACT GAA AGA GTG ACT TTG ACA AGA TGT TTC TAC CTC         1200
Gln Met Pro Thr Thr Glu Arg Val Thr Leu Thr Arg Cys Phe Tyr Leu
385                 390                 395                 400

TTC CCA GGA CAT TAA                                                     1215
Phe Pro Gly His
```

(2) INFORMATION FOR SEQ ID NO:18:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
        50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
290                 295                 300

Leu Ser Leu Pro Thr Thr Glu Glu Phe Glu Asp Asp Ala Ile Lys Lys
```

```
                                    -continued 305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
                340                 345                 350

Leu Ile Glu His Met Gln Glu Tyr Ala Cys Ser Cys Asp Val Glu Glu
                355                 360                 365

Ile Phe Arg Lys Val Arg Phe Ser Phe Glu Gln Pro Asp Gly Arg Ala
                370                 375                 380

Gln Met Pro Thr Thr Glu Arg Val Thr Leu Thr Arg Cys Phe Tyr Leu
385                 390                 395                 400

Phe Pro Gly His
```